US010251392B2

(12) United States Patent
Karandikar et al.

(10) Patent No.: US 10,251,392 B2
(45) Date of Patent: *Apr. 9, 2019

(54) ANTIMICROBIAL DEVICES AND COMPOSITIONS

(75) Inventors: Bhalchandra M. Karandikar, Tigard, OR (US); Bruce L. Gibbins, Lake Oswego, OR (US); Ken A. Cornell, Meridian, ID (US)

(73) Assignee: Avent, Inc., Alpharetta, GA (US)

( * ) Notice: Subject to any disclaimer, the term of this patent is extended or adjusted under 35 U.S.C. 154(b) by 2146 days.

This patent is subject to a terminal disclaimer.

(21) Appl. No.: 11/572,899

(22) PCT Filed: Aug. 1, 2005

(86) PCT No.: PCT/US2005/027260
§ 371 (c)(1),
(2), (4) Date: May 13, 2008

(87) PCT Pub. No.: WO2006/015317
PCT Pub. Date: Feb. 9, 2006

(65) Prior Publication Data
US 2009/0035342 A1    Feb. 5, 2009

Related U.S. Application Data

(60) Provisional application No. 60/592,535, filed on Jul. 30, 2004.

(51) Int. Cl.
| | | |
|---|---|---|
| *A01N 25/04* | (2006.01) |
| *A01N 25/34* | (2006.01) |
| *A01N 43/80* | (2006.01) |
| *A01N 59/16* | (2006.01) |
| *A01N 59/20* | (2006.01) |
| *A61L 15/46* | (2006.01) |
| *A61L 27/54* | (2006.01) |
| *A61L 29/16* | (2006.01) |

(52) U.S. Cl.
CPC ............ *A01N 25/34* (2013.01); *A01N 59/16* (2013.01); *A61L 15/46* (2013.01); *A61L 27/54* (2013.01); *A61L 29/16* (2013.01); *A61L 2300/102* (2013.01); *A61L 2300/104* (2013.01); *A61L 2300/404* (2013.01)

(58) Field of Classification Search
CPC ........ A01N 59/16; A01N 25/34; A01N 25/04; A01N 43/80; A61L 15/46; A61L 2300/102; A61L 2300/104; A61L 2300/404; A61L 27/54; A61L 29/16
See application file for complete search history.

(56) References Cited

U.S. PATENT DOCUMENTS

| | | |
|---|---|---|
| 2,396,515 A | 3/1946 | Kreidl et al. |
| 2,934,066 A | 4/1960 | Stowasser et al. |
| 3,092,552 A | 6/1963 | Romans |
| 3,152,094 A | 10/1964 | Erner et al. |
| 3,152,904 A | 10/1964 | Sorensen et al. |
| 3,157,524 A | 11/1964 | Artandi |
| 3,485,658 A | 12/1969 | Iler |
| 3,511,764 A | 5/1970 | Marans et al. |
| 3,624,835 A | 11/1971 | Wyatt |
| 3,645,835 A | 2/1972 | Hodgson |
| 3,647,439 A | 3/1972 | Bass |
| 3,846,236 A | 11/1974 | Updike et al. |
| 3,933,507 A | 1/1976 | Von Konig et al. |
| 3,969,498 A | 7/1976 | Catania et al. |
| 3,996,141 A | 12/1976 | Updike |
| 4,113,658 A | 9/1978 | Geus |
| 4,130,517 A | 12/1978 | Lundberg et al. |
| 4,136,177 A | 1/1979 | Lin et al. |
| 4,136,178 A | 1/1979 | Lin et al. |
| 4,173,482 A * | 11/1979 | Akashi et al. ............... 430/619 |
| 4,260,677 A | 4/1981 | Winslow et al. |
| 4,306,551 A | 12/1981 | Hymes et al. |
| 4,310,509 A | 1/1982 | Berglund et al. |
| 4,320,201 A | 3/1982 | Berg et al. |
| 4,328,799 A | 5/1982 | LoPiano |
| 4,340,043 A | 7/1982 | Seymour |
| 4,364,929 A | 12/1982 | Sasmor et al. |
| 4,393,048 A | 7/1983 | Mason, Jr. et al. |
| 4,474,571 A | 10/1984 | Lasley |
| 4,483,688 A | 11/1984 | Akiyama |
| 4,529,623 A | 7/1985 | Maggs |
| 4,604,384 A | 8/1986 | Smith et al. |
| 4,608,041 A | 8/1986 | Nielsen |

(Continued)

FOREIGN PATENT DOCUMENTS

| | | |
|---|---|---|
| EP | 0072251 A2 | 2/1983 |
| EP | 0297769 A1 | 1/1989 |

(Continued)

OTHER PUBLICATIONS

Baran et al. Vibrational spectra of silver saccharinate, Journal of Raman Spectroscopy, 2001, 32, 1064-1066.*

(Continued)

*Primary Examiner* — Kortney L. Klinkel
(74) *Attorney, Agent, or Firm* — Dority & Manning, P.A.

(57) ABSTRACT

The present invention comprises methods and compositions for antimicrobial devices comprising metal containing compositions which are resistant to heat and light discoloration. The metal containing compositions may comprise salts or complexes of silver, copper or zinc. In one aspect the compositions comprise silver salts. In another aspect, the compositions comprise silver complexes. In one aspect, the metal salts may comprise metal salts of saccharin, acesulfame, long chain fatty acids, and alkyl dicarboxylic acids. The compositions further comprise polymers which form salts or complexes with silver, copper or zinc. The methods of the present invention comprise treating devices with the metal containing compositions, including, but not limited to, such devices as woven wound care materials, catheters, patient care devices, and collagen matrices. The present invention further comprises treatment of humans and animals with the antimicrobial devices described herein.

13 Claims, No Drawings

(56) References Cited

U.S. PATENT DOCUMENTS

| | | |
|---|---|---|
| 4,612,337 A | 9/1986 | Fox, Jr. et al. |
| 4,624,656 A | 11/1986 | Clark et al. |
| 4,686,211 A | 8/1987 | Hara et al. |
| 4,708,821 A | 11/1987 | Shimokawa et al. |
| 4,721,724 A | 1/1988 | Stettendorf et al. |
| 4,747,847 A | 5/1988 | Magruder et al. |
| 4,782,819 A | 11/1988 | Adair |
| 4,801,291 A | 1/1989 | Loori |
| 4,902,503 A | 2/1990 | Umemura et al. |
| 4,915,694 A | 4/1990 | Yamamoto et al. |
| 4,969,881 A | 11/1990 | Viesturs |
| 5,023,082 A | 6/1991 | Friedman et al. |
| 5,049,139 A | 9/1991 | Gilchrist |
| 5,076,265 A | 12/1991 | Wokalek |
| 5,086,620 A | 2/1992 | Spears |
| 5,091,171 A | 2/1992 | Yu et al. |
| 5,100,668 A | 3/1992 | Edelman et al. |
| 5,128,326 A | 7/1992 | Balazs et al. |
| 5,149,524 A | 9/1992 | Sherba et al. |
| 5,151,271 A | 9/1992 | Otsuka et al. |
| 5,158,772 A | 10/1992 | Davis |
| 5,175,229 A | 12/1992 | Braatz et al. |
| 5,181,914 A | 1/1993 | Zook |
| 5,196,190 A | 3/1993 | Nangia et al. |
| 5,236,421 A | 8/1993 | Becher |
| 5,270,358 A | 12/1993 | Asmus |
| 5,326,567 A * | 7/1994 | Capelli .................. 424/405 |
| 5,342,528 A | 8/1994 | Adachi et al. |
| 5,354,862 A | 10/1994 | Hsu |
| 5,407,685 A | 4/1995 | Malchesky et al. |
| 5,429,591 A | 7/1995 | Yamamoto et al. |
| 5,432,077 A | 7/1995 | Farrah |
| 5,447,492 A | 9/1995 | Cartmell et al. |
| 5,453,401 A | 9/1995 | Grivna et al. |
| 5,454,886 A | 10/1995 | Burrell et al. |
| 5,464,610 A | 11/1995 | Hayes, Jr. et al. |
| 5,470,585 A | 11/1995 | Gilchrist |
| 5,503,840 A | 4/1996 | Jacobson et al. |
| 5,508,038 A | 4/1996 | Wang et al. |
| 5,508,417 A | 4/1996 | Osei-Gyimah et al. |
| 5,516,502 A | 5/1996 | Dickerson |
| 5,527,534 A | 6/1996 | Myhling |
| 5,567,495 A | 10/1996 | Modak et al. |
| 5,569,207 A | 10/1996 | Gisselberg et al. |
| 5,593,683 A | 1/1997 | Viegas et al. |
| 5,599,296 A | 2/1997 | Spears |
| 5,603,946 A | 2/1997 | Constantine |
| 5,614,568 A | 3/1997 | Mawatari et al. |
| 5,651,978 A | 7/1997 | Tomioka et al. |
| 5,660,854 A | 8/1997 | Haynes et al. |
| 5,681,579 A | 10/1997 | Freeman |
| 5,683,713 A | 11/1997 | Blank et al. |
| 5,693,624 A | 12/1997 | Hardy et al. |
| 5,695,777 A | 12/1997 | Donovan et al. |
| 5,709,870 A | 1/1998 | Yoshimura et al. |
| 5,725,491 A | 3/1998 | Tipton et al. |
| 5,735,251 A | 4/1998 | Hyodo et al. |
| 5,736,582 A | 4/1998 | Devillez |
| 5,744,151 A | 4/1998 | Capelli |
| 5,753,251 A | 5/1998 | Burrell et al. |
| 5,792,090 A | 8/1998 | Ladin |
| 5,804,213 A | 9/1998 | Rolf |
| 5,820,918 A | 10/1998 | Ronan et al. |
| 5,830,496 A | 11/1998 | Freeman |
| 5,833,665 A | 11/1998 | Bootman et al. |
| 5,840,283 A | 11/1998 | Sorenson et al. |
| 5,853,742 A | 12/1998 | Bartolone et al. |
| 5,855,570 A | 1/1999 | Scherson et al. |
| 5,863,548 A | 1/1999 | Elder |
| 5,863,864 A | 1/1999 | Plath et al. |
| 5,869,073 A | 2/1999 | Sawan et al. |
| 5,908,693 A | 6/1999 | Delgado et al. |
| 5,927,317 A | 7/1999 | Hsia |
| 5,928,174 A | 7/1999 | Gibbins |
| 5,951,458 A | 9/1999 | Hastings et al. |
| 5,961,996 A | 10/1999 | Garson et al. |
| 5,965,204 A | 10/1999 | Sodervall et al. |
| 5,972,317 A | 10/1999 | Sorenson et al. |
| 5,993,790 A | 11/1999 | Strauss |
| 6,000,403 A | 12/1999 | Cantwell |
| 6,004,667 A | 12/1999 | Sakurada et al. |
| 6,011,194 A | 1/2000 | Buglino et al. |
| 6,014,585 A | 1/2000 | Stoddard |
| 6,042,845 A | 3/2000 | Sun et al. |
| 6,051,614 A | 4/2000 | Hirai et al. |
| 6,099,805 A | 8/2000 | Hartlove |
| 6,103,868 A | 8/2000 | Heath et al. |
| 6,110,447 A | 8/2000 | Ramin et al. |
| 6,113,287 A | 9/2000 | Merz et al. |
| 6,143,794 A | 11/2000 | Chaudhuri et al. |
| 6,159,977 A | 12/2000 | Reeves |
| 6,187,290 B1 | 2/2001 | Gilchrist et al. |
| 6,191,339 B1 | 2/2001 | Gueret |
| 6,201,164 B1 | 3/2001 | Wulff et al. |
| 6,214,360 B1 | 4/2001 | Richter et al. |
| 6,224,622 B1 | 5/2001 | Kotzev |
| 6,231,840 B1 | 5/2001 | Buck |
| 6,235,964 B1 | 5/2001 | Kadash et al. |
| 6,248,342 B1 | 6/2001 | Trogolo et al. |
| 6,264,927 B1 | 7/2001 | Monahan |
| 6,270,811 B1 | 8/2001 | Fregonese |
| 6,316,084 B1 | 11/2001 | Claus et al. |
| 6,326,524 B1 | 12/2001 | Fattman et al. |
| 6,355,858 B1 | 3/2002 | Gibbins |
| 6,468,989 B1 | 10/2002 | Chang et al. |
| 6,471,982 B1 | 10/2002 | Lydon et al. |
| 6,530,895 B1 | 3/2003 | Keirn |
| 6,596,906 B2 | 7/2003 | Baumann et al. |
| 6,605,751 B1 | 8/2003 | Gibbins et al. |
| 6,669,981 B2 | 12/2003 | Parsons et al. |
| 6,716,895 B1 | 4/2004 | Terry |
| 6,897,349 B2 | 5/2005 | Gibbins et al. |
| 6,921,529 B2 | 7/2005 | Maley |
| 7,129,389 B1 | 10/2006 | Watson |
| 7,160,553 B2 | 1/2007 | Gibbins et al. |
| 7,166,330 B2 | 1/2007 | Takahashi et al. |
| 7,189,410 B1 | 3/2007 | Drohan et al. |
| 7,576,255 B2 | 8/2009 | Gibbins et al. |
| 2001/0026810 A1 | 10/2001 | McGhee et al. |
| 2001/0041188 A1 | 11/2001 | Gibbins et al. |
| 2002/0001604 A1 | 1/2002 | Shigeru et al. |
| 2002/0042587 A1 | 4/2002 | Murdock |
| 2002/0073891 A1 | 6/2002 | Parsons et al. |
| 2002/0082340 A1 | 6/2002 | Hanke et al. |
| 2003/0041188 A1 | 2/2003 | Han et al. |
| 2003/0083610 A1 | 5/2003 | McGrath et al. |
| 2003/0093057 A1 | 5/2003 | Zhang et al. |
| 2003/0186955 A1 | 10/2003 | Vange et al. |
| 2004/0010215 A1 | 1/2004 | Gibbins et al. |
| 2004/0082925 A1 | 4/2004 | Patel |
| 2004/0096410 A1 | 5/2004 | Maley et al. |
| 2004/0108462 A1 | 6/2004 | Besesty et al. |
| 2004/0127025 A1 | 7/2004 | Crocker et al. |
| 2004/0147618 A1 | 7/2004 | Lee et al. |
| 2004/0170545 A1 | 9/2004 | Emanuel |
| 2004/0173056 A1 | 9/2004 | McNally et al. |
| 2004/0180093 A1 | 9/2004 | Burton et al. |
| 2004/0253536 A1 | 12/2004 | Park et al. |
| 2004/0254532 A1 | 12/2004 | Mehier |
| 2005/0008861 A1 | 1/2005 | Yadav et al. |
| 2005/0029121 A1 | 2/2005 | Monzyk et al. |
| 2005/0186135 A1 | 8/2005 | Howes |
| 2005/0265894 A1 | 12/2005 | Monzyk et al. |
| 2006/0276740 A1 | 12/2006 | Bagley |
| 2007/0003603 A1 | 1/2007 | Karandikar et al. |
| 2007/0207335 A1 | 9/2007 | Karandikar et al. |
| 2007/0254044 A1 | 11/2007 | Karandikar et al. |
| 2007/0293800 A1 | 12/2007 | McMaken et al. |
| 2010/0034882 A1 | 2/2010 | Gibbins et al. |

FOREIGN PATENT DOCUMENTS

| | | |
|---|---|---|
| EP | 0489206 A1 | 6/1992 |
| EP | 0500387 | 8/1992 |

(56) References Cited

FOREIGN PATENT DOCUMENTS

| | | |
|---|---|---|
| EP | 0707793 A1 | 4/1996 |
| EP | 0709101 A2 | 5/1996 |
| EP | 1190622 A1 | 3/2002 |
| EP | 1245239 A1 | 10/2002 |
| EP | 1388561 A2 | 2/2004 |
| GB | 847256 | 7/1960 |
| GB | 863875 | 3/1961 |
| GB | 1471013 A | 4/1977 |
| GB | 1554002 A | 10/1979 |
| GB | 2024012 A | 1/1980 |
| GB | 2134791 A | 8/1984 |
| JP | 05-271718 A | 10/1993 |
| JP | 6248549 A | 9/1994 |
| JP | 7097767 A | 4/1995 |
| JP | 11302119 A | 11/1999 |
| JP | 2000256102 | 3/2000 |
| JP | 2003529630 A | 10/2003 |
| JP | 2004124300 | 4/2004 |
| JP | 2004137615 A | 5/2004 |
| JP | 2004161632 A | 6/2004 |
| WO | WO-84/01721 A1 | 5/1984 |
| WO | WO-88/06894 A1 | 9/1988 |
| WO | WO-90/03810 A1 | 4/1990 |
| WO | WO-96/11572 A1 | 4/1996 |
| WO | WO-98/06260 A1 | 2/1998 |
| WO | WO-98/20719 A1 | 5/1998 |
| WO | 1999/15101 | 4/1999 |
| WO | WO-99/25395 A2 | 5/1999 |
| WO | WO-00/09173 A1 | 2/2000 |
| WO | WO-00/15202 A2 | 3/2000 |
| WO | WO-01/011955 A2 | 2/2001 |
| WO | WO-01/024839 A1 | 4/2001 |
| WO | WO-01/049258 A2 | 7/2001 |
| WO | WO-0226039 A1 | 4/2002 |
| WO | WO0230204 A1 | 4/2002 |
| WO | WO-0243743 A1 | 6/2002 |
| WO | WO-02/061403 A1 | 8/2002 |
| WO | WO-02/076518 A1 | 10/2002 |
| WO | WO-03/002089 A1 | 1/2003 |
| WO | WO-03/080231 A1 | 10/2003 |
| WO | WO-04/001880 A1 | 12/2003 |
| WO | WO-04/010952 A2 | 2/2004 |
| WO | WO-04/028255 A1 | 4/2004 |
| WO | WO-04/056404 A2 | 7/2004 |
| WO | WO-06/026026 A2 | 3/2006 |
| WO | WO-06/034249 A2 | 3/2006 |
| WO | WO-07/095058 A2 | 8/2007 |
| WO | WO-07/127236 A2 | 11/2007 |
| WO | WO-08/131070 A1 | 10/2008 |

OTHER PUBLICATIONS

Bharathi, Subramanian et al., "Sol-Gel-Derived Nanocrystalline Gold-Silicate Composite Biosensor," Analytical Communications, 1998, 35: 29-31.
Chase, Grafton D., Pharmaceutical Science by Remington, 14th Edition., Mack Publishing Co., Rheology, Newtonian Flow-Plastic Flow-Pseudoplastic Flow-Dilatant Flow-Methods for Measuring Viscosity-Polymer Solutions-Thixotrophy-Pharmaceutical Applications, 1970, 359-371.
ConvaTec Corp. Aquacel Ag Product Info from website. [internet citation] Retrieved Dec. 9, 2002 from http://www.convatec.com/en_US/company/pr/index.html.
Cooper, Rose, "A Review of the Evidence for the Use of Topical Antimicrobial Agents in Wound Care," World Wide Wounds, 2004, 1-15.
FDA Approval Letter to begin OxyGenesis marketing. Sep. 19, 2008.
Feng et al, "Study of the initiation mechanism of the vinyl polymerization with the system persulfate/N,N,N',N'-tetramethylethylenediamine," Makromol. Chem. 1988, 189: 77-83.
Fox, Jr., Charles L., "Silver Sulfadiazine-A New Topical", Arch. Surg., vol. 96, pp. 184-188, 1968.

Gibbins et al., AcryDerm Absorbent Oxygen Dressing Point of Use Evaluation: Summary of Results. DRAFT. Jul. 17, 2009.
Gibbins, B. and Hopman, L., "A Comparison of a New Anti-Microbial Polyacrylate Absorbent Wound Dressing Containing Silver with the Silver-containing Anti-microbial Film Dressings", Presentation at Clinical Symposium on Wound Care, Oct. 2, 1999.
Gibbins, Bruce, "The Antimicrobial Benefits of Silver and the Relevance of Microlattice Technology," Ostomy Wound Manage. Feb. 2003; Suppl:4-7.
Grier, N., "Silver and Its Compounds," Disinfection, Sterilization, and Preservation, 3rd Edition. Seymour S. Block, ed., Lea & Febiger, Philadelphia, 1983; Chapter 18, pp. 375-389.
Hackh's Chemical Dictionary, 4th Edition, McGraw Hill Book Co., New York, 1969; p. 451.
Handbook of Common Polymers, "Polyvinyl Alcohol Including Insolubilised Fibres," Scott & Roff, Jr., W.J., The Chemical Company, 1971, pp. 72-197.
Jia et al., "Effect of locally released oxygen on wound healing," Presented at 18th Annual Meeting of the Wound Healing Society, San Diego, CA. Apr. 2008.
Junhui He et al, "Facile in situ synthesis of noble metal nanoparticles in porous cellulose fibers," Chemistry of Materials, 2003, 15(23): 4401-4406.
Kapoor, Sudhir, "Preparation, Characterization, and Surface Modification of Silver Particles," Langmuir, 1998, 14 (5):1021-1025.
Milk Composition & Synthesis Resourse Library, Milk Composition-Minerals [retrieved on Dec. 5, 2010], retrieved from the internet:<URL:http://ciasses.ansci.illinois.edu/ansc438/milkcompsynth/milkcomp_minerals.html>.
OxyGenesis Dissolved Oxygen Dressings: Case Review, AcryMed, Inc., Jan. 23, 2010.
Pepe, R.C, Wenninger, J.A., & McEwen, G.N., eds., Int'l Cosmetic Ingredient Dictionary & Handbook, 9th ed., 2002, vol. 2. pp. 177.
Price, William R. et al., "Silver Nitrate Burn Dressing, Treatment of Seventy Burned Persons," American Journal of Surgery, 1966, 112:674-680.
Ratner, Buddy D. et al., ACS Symposium Series, No. 31, The American Chemical Society, Synthetic Hydrogels for Biomedical Applications, pp. 1-36.
Rifai et al., "Facile in Situ Silver Nanoparticle Formation in Insulating Porous Polymer Matrices," Chemistry of Materials 2006; 18(1): 21-25.
Roe, David F., Gibbins, Bruce L., and Ladizinsky, Daniel A., "Topical Dissolved Oxygen Penetrates Skin: Model and Method," J Surg Res. 2010, 159(1):e29-e36.
Russel A. and Hugo, W., "Antimicrobial Activity and Action of Silver," Progress in Medicinal Chemistry, vol. 31, G-.P. Ellis & D.K. Luscombe, ed., Elsevier Science B.V., 1994; pp. 351-370.
Schacht, Etienne H., Hydrogel Drug Delivery Systems, Institute of Organic Chemistry, State University Gent, 1984, pp. 259-278.
Sheehan et al, "Anti-bacterial Silver Coatings on Orthopaedic Metals—An In Vitro and Animal Study," Journal of Bone and Joint Surgery. 2003, 85-B(SUPP_II):141.
Silver, Simon, "Bacterial Silver Resistance: Molecular Biology and Uses and Misuses of Silver Compounds," FEMS Microbiology Reviews, 2003, pp. 341-353.
Topical Delivery Methods, undated reference, retrieved from file on May 11, 2011.
Wang et al., "Directing oleate stabilized nanosized silver colloids into organic phases", Langmuir: The ACS Journal of Surfaces and Colloids. 1998; 14:602-610.
Communication regarding the expiration of oppposition period dated Feb. 10, 2006 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Decision to grant a European Pat. dated Feb. 24, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Approval of request for amendments/corrections dated Feb. 15, 2005 for European Pat. App. No. 98961733.7 which claims priority

(56) References Cited

OTHER PUBLICATIONS to PCT/US98/024272 filed on Nov. 13, 1998, published May 27, 1999 as WO 99/027680 (Applicant—Acrymed; Inventors: B.L. Gibbins).
Reply to communication from the Examining Division filed on Dec. 22, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Result of Consultation by telephone/in person (with time limit) issued on Nov. 9, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Request for correction/amendment of the text proposed for grant filed on Oct. 26, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication about intention to grant a European Pat. dated Jun. 18, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on Aug. 20, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division dated May 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on Feb. 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division dated Aug. 1, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on May 20, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division dated Jul. 31, 2001 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
PCT Intl. Search Report dated Jun. 23, 1999 for PCT/US98/24272, filed on Nov. 13, 1998, published May 27, 1999 as WO 99/027680 (Applicant—Acrymed; Inventors: B.L. Gibbins).
PCT Intl. Preliminary exam report dated Aug. 8, 2001 for PCT/US98/24272, filed on Nov. 13, 1998, published May 27, 1999 as WO 99/027680 (Applicant—Acrymed; Inventors: B.L. Gibbins).
PCT Written opinion dated Feb. 18, 2000 for PCT/US98/24272, filed on Nov. 13, 1998, published May 27, 1999 as WO 99/027680 (Applicant—Acrymed; Inventors: B.L. Gibbins).
Issue Notification dated Jul. 14, 1999 for U.S. Appl. No. 08/971,074, filed Nov. 14, 1997 (Inventor—B.L. Gibbins).
Notice of Allowance dated Feb. 25, 1999 for U.S. Appl. No. 08/971,074, filed Nov. 14, 1997 (Inventor—B.L. Gibbins).
Examiner Interview Summary/Amendment dated Dec. 11, 1998 for U.S. Appl. No. 08/971,074, filed Nov. 14, 1997 (Inventor—B.L. Gibbins).
Response after Non-Final Action filed on Nov. 18, 1998 for U.S. Appl. No. 08/971,074 filed Nov. 14, 1997 (Inventor—B.L. Gibbins).
Non-Final Rejection dated Aug. 19, 1998 for U.S. Appl. No. 08/971,074 filed Nov. 14, 1997 (Inventor—B.L. Gibbins).
Response to Election / Restriction filed on Jul. 14, 1998 for U.S. Appl. No. 08/971,074, filed Nov. 14, 1997 (Inventor—B.L. Gibbins).
Restriction Requirement dated May 21, 1998 for U.S. Appl. No. 08/971,074, filed Nov. 14, 1997 (Inventor—B.L. Gibbins).
Issue Notification dated Mar. 12, 2002 for U.S. Appl. No. 09/191,223, filed Nov. 13, 1998 (Inventor—B.L. Gibbins).
Notice of Allowance dated Sep. 25, 2001 for U.S. Appl. No. 09/191,223, filed Nov. 13, 1998 (Inventor—B.L. Gibbins).
Notice of Allowance dated Oct. 3, 2000 for U.S. Appl. No. 09/191,223, filed Nov. 13, 1998 (Inventor—B.L. Gibbins).
Response after Non-Final Action filed on Aug. 11, 2000 for U.S. Appl. No. 09/191,223, filed Nov. 13, 1998 (Inventor—B.L. Gibbins).
Non-Final Rejection dated Apr. 11, 2000 for U.S. Appl. No. 09/191,223, filed Nov. 13, 1998 (Inventor—B.L. Gibbins).
Response to Election / Restriction filed on Mar. 21, 2000 for U.S. Appl. No. 09/191,223, filed Nov. 13, 1998 (Inventor—B.L. Gibbins).
Restriction Requirement dated Feb. 22, 2000 for U.S. Appl. No. 09/191,223, filed Nov. 13, 1998 (Inventor—B.L. Gibbins).
Communication regarding the expiry of opposition period issued on Sep. 2, 2009 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Decision to grant a European Pat. dated Oct. 2, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication about intention to grant a European Pat. dated Apr. 10, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Feb. 26, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division dated Oct. 18, 2007 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Dec. 28, 2006 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division dated Sep. 1, 2006 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Mar. 21, 2005 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division dated Sep. 20, 2004 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Feb. 27, 2003 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division dated Aug. 21, 2002 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
PCT Intl. Search Report dated Feb. 5, 2001 for PCT/US00/26890, filed on Sep. 29, 2000, published Apr. 12, 2001 as WO 01/24839 (Applicant—Acrymed; Inventors: Gibbins).
PCT Written Opinion dated Jul. 23, 2001 for PCT/US00/26890, filed on Sep. 29, 2000, published Apr. 12, 2001 as WO 01/24839 (Applicant—Acrymed; Inventors: Gibbins).

(56) References Cited

OTHER PUBLICATIONS

PCT Intl. Preliminary Examination Report dated Oct. 17, 2001 for PCT/US00/26890, filed on Sep. 29, 2000, published Apr. 12, 2001 as WO 01/24839 (Applicant—Acrymed; Inventors: Gibbins).
Notice of Allowance dated Apr. 15, 2003 for U.S. Appl. No. 09/675,892, filed Sep. 29, 2000 (Inventor—B.L. Gibbins).
Amendment/Response After Non-Final Rejection filed on Mar. 21, 2003 for U.S. Appl. No. 09/675,892, filed Sep. 29, 2000 (Inventor—B.L. Gibbins).
Non-Final Rejection dated Nov. 21, 2002 for U.S. Appl. No. 09/675,892, filed Sep. 29, 2000 (Inventor—B.L. Gibbins).
Amendment After Final filed on Oct. 30, 2002 for U.S. Appl. No. 09/675,892, filed Sep. 29, 2000 (Inventor—B.L. Gibbins).
Final Rejection dated Jul. 31, 2002 for U.S. Appl. No. 09/675,892, filed Sep. 29, 2000 (Inventor—B.L. Gibbins).
Amendment/Response After Non-Final Rejection filed on Apr. 18, 2002 for U.S. Appl. No. 09/675,892, filed Sep. 29, 2000 (Inventor—B.L. Gibbins).
Non-Final Rejection dated Jan. 18, 2002 for U.S. Appl. No. 09/675,892, filed Sep. 29, 2000 (Inventor—B.L. Gibbins).
Notice of Allowance dated Mar. 7, 2005 for U.S. Appl. No. 10/441,275, filed May 19, 2003 (Inventor—B.L. Gibbins).
Notice of Allowance/Examiner Interview Summary Record dated Jul. 2, 2004 for U.S. Appl. No. 10/441,275, filed May 19, 2003 (Inventor—B.L. Gibbins).
Examiner Interview Summary Record (PTOL-413) dated May 26, 2004 for U.S. Appl. No. 10/441,275, filed May 19, 2003 (Inventor—B.L. Gibbins).
Supplemental Preliminary Amendment filed on Mar. 25, 2004 for U.S. Appl. No. 10/441,275, filed May 19, 2003 (Inventor—B.L. Gibbins).
Preliminary Amendment filed on Dec. 2, 2003 for U.S. Appl. No. 10/441,275, filed May 19, 2003 (Inventor—B.L. Gibbins).
Issue Notification dated Jul. 29, 2009 for U.S. Appl. No. 10/978,556, filed Nov. 1, 2004 (Inventor—B.L. Gibbins).
Notice of Allowance dated Apr. 16, 2009 for U.S. Appl. No. 10/978,556, filed Nov. 1, 2004 (Inventor—B.L. Gibbins).
Terminal Disclaimer/Amendment After Final Rejection filed on Apr. 6, 2009 for U.S. Appl. No. 10/978,556, filed Nov. 1, 2004 (Inventor—B.L. Gibbins).
Final Rejection dated Nov. 6, 2008 for U.S. Appl. No. 10/978,556, filed Nov. 1, 2004 (Inventor—B.L. Gibbins).
Amendment/Response After Non-Final Rejection filed on Aug. 1, 2008 for U.S. Appl. No. 10/978,556, filed Nov. 1, 2004 (Inventor—B.L. Gibbins).
Non-Final Rejection dated Apr. 1, 2008 for U.S. Appl. No. 10/978,556, filed Nov. 1, 2004 (Inventor—B.L. Gibbins).
Amendment Submitted/Entered with CPA/RCE filed on Oct. 31, 2007 for U.S. Appl. No. 10/978,556, filed Nov. 1, 2004 (Inventor—B.L. Gibbins).
Advisory Action (PTOL-303) dated Oct. 3, 2007 for U.S. Appl. No. 10/978,556, filed Nov. 1, 2004 (Inventor—B.L. Gibbins).
Amendment After Final Rejection filed on Sep. 13, 2007 for U.S. Appl. No. 10/978,556, filed Nov. 1, 2004 (Inventor—B.L. Gibbins).
Final Rejection dated Jul. 13, 2007 for U.S. Appl. No. 10/978,556, filed Nov. 1, 2004 (Inventor—B.L. Gibbins).
Amendment/Response After Non-Final Rejection filed on Apr. 24, 2007 for U.S. Appl. No. 10/978,556, filed Nov. 1, 2004 (Inventor—B.L. Gibbins).
Non-Final Rejection dated Jan. 24, 2007 for U.S. Appl. No. 10/978,556, filed Nov. 1, 2004 (Inventor—B.L. Gibbins).
Response to Election / Restriction filed on Nov. 13, 2006 for U.S. Appl. No. 10/978,556, filed Nov. 1, 2004 (Inventor—B.L. Gibbins).
Requirement for Restriction/Election dated Oct. 11, 2006 for U.S. Appl. No. 10/978,556, filed Nov. 1, 2004 (Inventor—B.L. Gibbins).
Preliminary Amendment filed on Feb. 15, 2005 for U.S. Appl. No. 10/978,556, filed Nov. 1, 2004 (Inventor—B.L. Gibbins).
Reexamination Certificate Issued on Jun. 16, 2009 for Inter Partes Reexam No. 95/000,042 of U.S. Pat. No. 6,605,751 granted Aug. 12, 2003 (Gibbins et al.).
Notice of Intent to Issue a Reexam Certificate issued on Mar. 25, 2009 for Inter Partes Reexam No. 95/000,042 of U.S. Pat. 6,605,751 granted Aug. 12, 2003 (Gibbins et al.).
Right of Appeal Notice issued on Dec. 9, 2008 for Inter Partes Reexam No. 95/000,042 of U.S. Pat. No. 6,605,751 granted Aug. 12, 2003 (Gibbins et al.).
Action Closing Prosecution (nonfinal) issued on Aug. 19, 2008 for Inter Partes Reexam No. 95/000,042 of U.S. Pat. No. 6,605,751 granted Aug. 12, 2003 (Gibbins et al.).
Response after non-final action-owner filed on Oct. 8, 2004 for Inter Partes Reexam No. 95/000,042 of U.S. Pat. No. 6,605,751 granted Aug. 12, 2003 (Gibbins et al.).
Reexam Ordered and Non-Final Action issued on Aug. 4, 2004 for Inter Partes Reexam No. 95/000,042 of U.S. Pat. No. 6,605,751 granted Aug. 12, 2003 (Gibbins et al.).
Ex Parte Reexam request filed on May 13, 2004 for Inter Partes Reexam No. 95/000,042 of U.S. Pat. No. 6,605,751 granted Aug. 12, 2003 (Gibbins et al.).
Notice of Allowance dated May 12, 2011 for U.S. Appl. No. 12/510,651, filed Jul. 28, 2009 (Inventor—Gibbins).
Amendment/Response After Non-Final Reject/Terminal Disclaimer filed on Apr. 4, 2011 for U.S. Appl. No. 12/510,651, filed Jul. 28, 2009 (Inventor—Gibbins).
Non-Final Rejection dated Jan. 5, 2011 for U.S. Appl. No. 12/510,651, filed Jul. 28, 2009 (Inventor—Gibbins).
Preliminary Amendment filed on Oct. 28, 2009 for U.S. Appl. No. 12/510,651, filed Jul. 28, 2009 (Inventor—Gibbins).
Communication regarding the expiry of opposition period issued on Apr. 4, 2007 for EP App. No. 990393.1, which claims priority to PCT/US00/35560, filed on Dec. 29, 2000, published Jul. 12, 2001 as WO 01/49258 (Applicant—Acrymed).
Decision to grant a European Pat. dated Apr. 21, 2006 for EP App. No. 990393.1, which claims priority to PCT/US00/35560, filed on Dec. 29, 2000, published Jul. 12, 2001 as WO 01/49258 (Applicant—Acrymed).
Reply to communication about intention to grant filed on Mar. 28, 2006 for EP App. No. 990393.1, which claims priority to PCT/US00/35560, filed on Dec. 29, 2000, published Jul. 12, 2001 as WO 01/49258 (Applicant—Acrymed).
Communication about intention to grant a European Pat. filed on Nov. 28, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Aug. 30, 2005 for EP App. No. 990393.1, which claims priority to PCT/US00/35560, filed on Dec. 29, 2000, published Jul. 12, 2001 as WO 01/49258 (Applicant—Acrymed).
Communication from the Examining Division dated Feb. 22, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Apr. 1, 2004 for EP App. No. 990393.1, which claims priority to PCT/US00/35560, filed on Dec. 29, 2000, published Jul. 12, 2001 as WO 01/49258 (Applicant—Acrymed).
Communication from the Examining Division dated Feb. 13, 2004 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Jul. 24, 2003 for EP App. No. 990393.1, which claims priority to PCT/US00/35560, filed on Dec. 29, 2000, published Jul. 12, 2001 as WO 01/49258 (Applicant—Acrymed).
Communication from the Examining Division dated Jan. 23, 2003 for EP App. No. 990393.1, which claims priority to PCT/US00/35560, filed on Dec. 29, 2000, published Jul. 12, 2001 as WO 01/49258 (Applicant—Acrymed).
Amendments before examination filed on Oct. 18, 2002 for EP App. No. 990393.1, which claims priority to PCT/US00/35560, filed on Dec. 29, 2000, published Jul. 12, 2001 as WO 01/49258 (Applicant—Acrymed).

(56) References Cited

OTHER PUBLICATIONS

Amendments before examination filed on Jul. 19, 2002 for EP App. No. 990393.1, which claims priority to PCT/US00/35560, filed on Dec. 29, 2000, published Jul. 12, 2001 as WO 01/49258 (Applicant—Acrymed).
PCT Intl. Search Report dated Jul. 12, 2001 for PCT/US00/35560, filed on Dec. 29, 2000, published Jul. 12, 2001 as WO 01/49258 (Applicant—Acrymed; Inventors: Gibbins).
PCT Intl. Preliminary Examination Report dated Apr. 2, 2002 for PCT/US00/35560, filed on Dec. 29, 2000, published Jul. 12, 2001 as WO 01/49258 (Applicant—Acrymed; Inventors: Gibbins).
Issue Notification dated Dec. 20, 2006 for U.S. Appl. No. 10/441,141, filed May 19, 2003 (Inventor—Gibbins).
Notice of Allowance/Examiner Interview Summary Record (PTOL-413) dated Jul. 25, 2006 for U.S. Appl. No. 10/441,141, filed May 19, 2003 (Inventor—Gibbins).
Amendment After Final Rejection filed on Jul. 5, 2006 for U.S. Appl. No. 10/441,141, filed May 19, 2003 (Inventor—Gibbins).
Examiner Interview Summary Record (PTOL-413) dated Jun. 28, 2006 for U.S. Appl. No. 10/441,141, filed May 19, 2003 (Inventor—Gibbins).
Final Rejection dated May 4, 2006 for U.S. Appl. No. 10/441,141, filed May 19, 2003 (Inventor—Gibbins).
Amendment/Response After Non-Final Action filed on Feb. 14, 2006 for U.S. Appl. No. 10/441,141, filed May 19, 2003 (Inventor—Gibbins).
Non-Final Rejection dated Nov. 15, 2005 for U.S. Appl. No. 10/441,141, filed May 19, 2003 (Inventor—Gibbins).
Preliminary Amendment filed on Apr. 12, 2003 for U.S. Appl. No. 10/441,141, filed May 19, 2003 (Inventor—Gibbins).
Notification of Grant dated Feb. 5, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fifth Office Action filed on Jan. 7, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.) + claims in English.
Fifth Office Action dated Oct. 23, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fourth Office Action filed on Sep. 11, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.)—English translation only.
Fourth Office Action dated Apr. 17, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to third Office Action filed on Aug. 27, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.) claims in English.
Third Office Action dated Jun. 13, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to Second Office Action filed on Dec. 25, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
Second Office Action dated Aug. 10, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to first Office Action filed on Sep. 1, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.

First Office Action dated Apr. 21, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Decision to Grant pursuant to Article 97(2) EPC dated Dec. 2, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication under Rule 71(3) EPC dated Jun. 4, 2010 for EP App. No. 3772113.1, which claims priority to PCT/US03/023851 filed Jul. 29, 2003, published Feb. 5, 2004 as WO 04/010952 (Applicant—Acrymed, Inc.).
Letter during examination procedure after communication from the Examining Division filed on Jan. 19, 2010 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jan. 13, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division dated Jul. 3, 2009 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jul. 15, 2008 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division dated Jan. 10, 2008 for EP App. No. 3772113.1, which claims priority to PCT/US03/023851 filed Jul. 29, 2003, published Feb. 5, 2004 as WO 04/010952 (Applicant—Acrymed, Inc.).
Supplementary European search report dated Dec. 14, 2006 for EP App. No. 3772113.1, which claims priority to PCT/US03/023851 filed Jul. 29, 2003, published Feb. 5, 2004 as WO 04/010952 (Applicant—Acrymed, Inc.).
Preliminary Amendment filed on Apr. 12, 2005 for EP App. No. 3772113.1, which claims priority to PCT/US03/023851 filed Jul. 29, 2003, published Feb. 5, 2004 as WO 04/010952 (Applicant—Acrymed, Inc.).
PCT Intl. Search Report dated Aug. 27, 2004 for Intl. App. No. PCT/US03/023851 filed Jul. 29, 2003, published Feb. 5, 2004 as WO 04/010952 (Applicant—AcryMed, Inc.).
Issue Notification dated Jul. 6, 2005 for U.S. Appl. No. 10/207,936, filed Jul. 29, 2002 (Inventor—Maley, J. C.).
Amendment/Response-After Non-Final Rejection filed on Apr. 25, 2005 for U.S. Appl. No. 10/207,936, filed Jul. 29, 2002 (Inventor—Maley, J. C.).
Office Communication dated Mar. 30, 2005 for U.S. Appl. No. 10/207,936, filed Jul. 29, 2002 (Inventor—Maley, J. C.).
Notice of Allowance and Fees Due (PTOL-85) with Examiner Interview Summary Record (PTOL—413) dated Feb. 16, 2005 for U.S. Appl. No. 10/207,936, filed Jul. 29, 2002 (Inventor—Maley, J. C.).
Supplemental Amendment after Final Rejection dated Jan. 28, 2005 for U.S. Appl. No. 10/207,936, filed Jul. 29, 2002 (Inventor—Maley, J. C.).
Response After Final Rejection filed on Jan. 12, 2005 for U.S. Appl. No. 10/207,936, filed Jul. 29, 2002 (Inventor—Maley, J. C.).
Final Rejection dated Nov. 23, 2004 for U.S. Appl. No. 10/207,936, filed Jul. 29, 2002 (Inventor—Maley, J. C.).
Response After Non-Final Rejection filed on Jul. 29, 2004 for U.S. Appl. No. 10/207,936, filed Jul. 29, 2002 (Inventor—Maley, J. C.).
Non-Final Rejection dated Apr. 29, 2004 for U.S. Appl. No. 10/207,936 filed Jul. 29, 2002 (Inventor—Maley, J. C.).
Response After Non-Final Rejection filed on Jan. 22, 2004 for U.S. Appl. No. 10/207,936, filed Jul. 29, 2002 (Inventor—Maley, J. C.).
Non-Final Rejection dated Oct. 22, 2003 for U.S. Appl. No. 10/207,936 filed Jul. 29, 2002 (Inventor—Maley, J. C.).
Non-Final Rejection dated Jun. 28, 2011 for U.S. Appl. No. 10/630,627, filed Jul. 29, 2003 (Inventor—Maley, J.C.).

(56) References Cited

OTHER PUBLICATIONS

Response After Non-Compliant Amendment filed on Jun. 2, 2010 for U.S. Appl. No. 10/630,627, filed Jul. 29, 2003 (Inventor—Maley, J.C.).
Amendment Submitted/Entered with CPA/RCE filed on Apr. 27, 2010 for U.S. Appl. No. 10/630,627, filed Jul. 29, 2003 (Inventor—Maley, J.C.).
Final Rejection dated Dec. 3, 2009 for U.S. Appl. No. 10/630,627, filed Jul. 29, 2003 (Inventor—Maley, J.C.).
Response After Non-Final Rejection filed on Jul. 20, 2009 for U.S. Appl. No. 10/630,627, filed Jul. 29, 2003 (Inventor—Maley, J.C.).
Non-Final Rejection dated Feb. 19, 2009 for U.S. Appl. No. 10/630,627, filed Jul. 29, 2003 (Inventor—Maley, J.C.).
Amendment Submitted/Entered with CPA/RCE filed on Nov. 26, 2008 for U.S. Appl. No. 10/630,627, filed Jul. 29, 2003 (Inventor—Maley, J.C.).
Final Rejection dated Jun. 26, 2008 for U.S. Appl. No. 10/630,627, filed Jul. 29, 2003 (Inventor—Maley, J.C.).
Response After Non-Final Rejection filed on Feb. 7, 2008 for U.S. Appl. No. 10/630,627, filed Jul. 29, 2003 (Inventor—Maley, J.C.).
Non-Final Rejection dated Sep. 7, 2007 for U.S. Appl. No. 10/630,627, filed Jul. 29, 2003 (Inventor—Maley, J.C.).
Amendment Submitted/Entered with CPA/RCE filed on Jun. 22, 2007 for U.S. Appl. No. 10/630,627, filed Jul. 29, 2003 (Inventor—Maley, J.C.).
Advisory Action (PTOL-303) dated May 17, 2007 for U.S. Appl. No. 10/630,627, filed Jul. 29, 2003 (Inventor—Maley, J.C.).
Amendment After Final Rejection filed on Apr. 23, 2007 for U.S. Appl. No. 10/630,627, filed Jul. 29, 2003 (Inventor—Maley, J.C.).
Final Rejection dated Feb. 23, 2007 for U.S. Appl. No. 10/630,627, filed Jul. 29, 2003 (Inventor—Maley, J.C.).
Response After Non-Final Rejection filed on Nov. 21, 2006 for U.S. Appl. No. 10/630,627, filed Jul. 29, 2003 (Inventor—Maley, J.C.).
Non-Final Rejection dated Aug. 24, 2006 for U.S. Appl. No. 10/630,627, filed Jul. 29, 2003 (Inventor—Maley, J.C.).
Response to Election / Restriction Filed on Jun. 23, 2006 for U.S. Appl. No. 10/630,627, filed Jul. 29, 2003 (Inventor—Maley, J.C.).
Restriction/Election Requirement dated May 23, 2006 for U.S. Appl. No. 10/630,627, filed Jul. 29, 2003 (Inventor—Maley, J.C.).
Response to First Office Action filed on Jul. 9, 2009 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.)—Proposed Claims in English.
First Office Action dated Dec. 26, 2008 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Amended claims filed on Feb. 26, 2007 for EP App. No. 05778379.7, which claims priority to Intl. App. No. PCT/US05/027260 filed Aug. 1, 2005, published Feb. 9, 2006 as WO 06/015317 (Applicant—Acrymed, Inc.).
Response to Examiners Report filed on Jun. 29, 2011 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Examiner's Report dated Jun. 29, 2010 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Intl. Preliminary Report on Patentability dated Jan. 30, 2007 for Intl. App. No. PCT/US05/027260 filed Aug. 1, 2005, published Feb. 9, 2006 as WO 06/015317 (Applicant—Acrymed, Inc.).
Intl. Search Report with Written Opinion dated Apr. 28, 2006 for Intl. App. No. PCT/US05/027260 filed Aug. 1, 2005, published Feb. 9, 2006 as WO 06/015317 (Applicant—Acrymed, Inc.).
Intl. Preliminary Report on Patentability dated Jan. 30, 2007 for Intl. App. No. PCT/US05/027261 filed Aug. 1, 2005, published Mar. 9, 2006 as WO 06/026026 (Applicant—Acrymed, Inc.).

Intl. Search Report with Written Opinion dated Apr. 28, 2006 for Intl. App. No. PCT/US05/027261 filed Aug. 1, 2005, published Mar. 9, 2006 as WO 06/026026 (Applicant—Acrymed, Inc.).
Notice of Acceptance dated Jan. 24, 2011 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Dec. 13, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Examiner's First Report dated Feb. 19, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
AU Divisional App. No. 2011202034 filed on May 3, 2011 from AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Second Office Action (Text Portion) dated Jun. 7, 2011 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Office Action filed on Jul. 9, 2009 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
First Office Action dated Dec. 26, 2008 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Jun. 30, 2011 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.)—proposed amendments only.
Examiner's Report dated Jul. 2, 2010 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.).
Official Action dated Mar. 1, 2011 for JP App. No. 2007-523881, which claims priority to Intl. Pat. App. No. PCT/US05/027261, filed on Aug. 1, 2005, published on Mar. 9, 2006 as WO 06/02026 (Applicant—Acrymed, Inc.)—translation included.
Notice of Acceptance dated Apr. 26, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Apr. 21, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report dated Feb. 2, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Jan. 20, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Further Examination Report dated Jul. 8, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response and Amended Pages filed on Jun. 28, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report dated Apr. 24, 2009 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).

(56) References Cited

OTHER PUBLICATIONS

NZ Divisional App. No. 592438 filed on Apr. 21, 2011 from New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Amendment Entered with CPA/RCE filed on Feb. 19, 2010 for U.S. Appl. No. 11/194,951, filed Aug. 1, 2005 (Inventor—Karandikar et al.).
Notice of Appeal filed on Oct. 21, 2009 for U.S. Appl. No. 11/194,951, filed Aug. 1, 2005 (Inventor—Karandikar et al.).
Final Rejection dated May 21, 2009 for U.S. Appl. No. 11/194,951, filed Aug. 1, 2005 (Inventor—Karandikar et al.).
Response After Non-Final Rejection filed on Feb. 5, 2009 for U.S. Appl. No. 11/194,951, filed Aug. 1, 2005 (Inventor—Karandikar et al.).
Non-Final Rejection dated Aug. 5, 2008 for U.S. Appl. No. 11/194,951, filed Aug. 1, 2005 (Inventor—Karandikar et al.).
Response to Election / Restriction filed on Feb. 5, 2008 for U.S. Appl. No. 11/194,951, filed Jan. 8, 2005 (Inventor —Karandikar et al.).
Requirement for Restriction/Election dated Dec. 5, 2007 for U.S. Appl. No. 11/194,951, filed Aug. 1, 2005 (Inventor—Karandikar et al.).
Examiner's first report dated Oct. 18, 2010 for Australian Pat. App. No. 2007215443, which claims priority to PCT/US07/03390, filed Feb. 8, 2007, published on Aug. 23, 2007 as WO 07/095058 (Applicant—Acrymed, Inc.).
Third Office Action dated Jul. 7, 2011 for Chinese Pat. App. No. 200780012684.5, which claims priority to PCT/US07/003390 filed on Feb. 8, 2007 (Applicant—AcryMed, Inc.).
Response to Second Office Action filed on Jun. 7, 2011 for Chinese Pat. App. No. 200780012684.5, which claims priority to PCT/US07/003390 filed on Feb. 8, 2007 (Applicant—AcryMed, Inc.)—No Translation.
Second Office Action dated Mar. 23, 2011 for Chinese Pat. App. No. 200780012684.5, which claims priority to PCT/US07/003390 filed on Feb. 8, 2007 (Applicant—AcryMed, Inc.).
Response to First Office Action filed on Feb. 28, 2011 for Chinese Pat. App. No. 200780012684.5, which claims priority to PCT/US07/003390 filed on Feb. 8, 2007 (Applicant—AcryMed, Inc.)—Proposed amended claims in English.
First Office Action dated Oct. 13, 2010 for Chinese Pat. App. No. 200780012684.5, which claims priority to PCT/US07/003390 filed on Feb. 8, 2007 (Applicant—AcryMed, Inc.).
Supplemental European Search Report dated May 23, 2011 for EP App. No. 07750244.1, which claims priority to PCT/US07/03390, filed Feb. 8, 2007, published on Aug. 23, 2007 as WO 07/095058 (Applicant—Acrymed, Inc.).
Claim amendments filed on Sep. 4, 2008 for EP App. No. 07750244.1, which claims priority to PCT/US07/03390, filed Feb. 8, 2007, published on Aug. 23, 2007 as WO 07/095058 (Applicant—Acrymed, Inc.).
PCT Preliminary Report on Patentability dated Aug. 12, 2008 for Intl. Pat. App. No. PCT/US07/03390, filed Feb. 8, 2007, published on Aug. 23, 2007 as WO 07/095058 (Applicant—Acrymed, Inc.).
PCT Intl. Search Report with Written Opinion dated Dec. 21, 2007 for Intl. Pat. App. No. PCT/US07/03390, filed Feb. 8, 2007, published on Aug. 23, 2007 as WO 07/095058 (Applicant—Acrymed, Inc.).
Non-Final Rejection dated Jun. 30, 2011 for U.S. Appl. No. 11/704,167, filed Feb. 8, 2007 (Inventors—Karandikar et al.).
Amendment Entered with CPA/RCE filed on Apr. 22, 2011 for U.S. Appl. No. 11/704,167, filed Feb. 8, 2007 (Inventors—Karandikar et al.).
Final Rejection dated Dec. 22, 2010 for U.S. Appl. No. 11/704,167, filed Feb. 8, 2007 (Inventors—Karandikar et al.).
Response after Non-Final Action dated Oct. 28, 2010 for U.S. Appl. No. 11/704,167, filed Aug. 2, 2007 (Inventors—Karandikar et al.).
Non-Final Rejection dated May 28, 2010 for U.S. Appl. No. 11/704,167, filed Feb. 8, 2007 (Inventors—Karandikar et al.).
Response to Election / Restriction filed on Apr. 30, 2010 for U.S. Appl. No. 11/704,167, filed Aug. 2, 2007 (Inventors—Karandikar et al.).
Restriction/Election Requirement dated Mar. 30, 2010 for U.S. Appl. No. 11/704,167, filed Feb. 8, 2007 (Inventors—Karandikar et al.).
Preliminary Amendments filed on Nov. 24, 2008 for EP 07755996.1 which claims priority to PCT/US07/009997, filed on Apr. 25, 2007, published on Nov. 8, 2007 as WO 07/127236 (Applicant—Acrymed, Inc.).
Intl. Search Report w/ Written Opinion dated Aug. 25, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability dated Oct. 28, 2008 for Intl. Pat. App. No. PCT/US07/009997, filed on Apr. 25, 2007, published on Nov. 8, 2007 as WO 07/127236 (Applicant—Acrymed, Inc.).
Final Rejection dated Jun. 23, 2011 for U.S. Appl. No. 11/789,701, filed Apr. 25, 2007 (Inventors—McMaken et al.).
Response after Non-Final Rejection filed on Apr. 5, 2011 for U.S. Appl. No. 11/789,701, filed Apr. 25, 2007 (Inventors—McMaken et al.).
Non-Final Rejection dated Oct. 5, 2010 for U.S. Appl. No. 11/789,701, filed Apr. 25, 2007 (Inventors—McMaken et al.).
Amendment Entered with CPA/RCE filed on Mar. 31, 2010 for U.S. Appl. No. 11/789,701, filed Apr. 25, 2007 (Inventors—McMaken et al.).
Final Rejection dated Oct. 5, 2009 for U.S. Appl. No. 11/789,701, filed Apr. 25, 2007 (Inventors—McMaken et al.).
Response After Non-Final Rejection filed Jun. 8, 2009 for U.S. Appl. No. 11/789,701, filed Apr. 25, 2007 (Inventors—McMaken et al.).
Non-Final Rejection dated Jan. 26, 2009 for U.S. Appl. No. 11/789,701, filed Apr. 25, 2007 (Inventors—McMaken et al.).
Response to Election / Restriction filed on Dec. 15, 2008 for U.S. Appl. No. 11/789,701, filed Apr. 25, 2007 (Inventors—McMaken et al.).
Requirement for Restriction/Election dated Nov. 14, 2008 for U.S. Appl. No. 11/789,701, filed Apr. 25, 2007 (Inventors—McMaken et al.).
Intl. Preliminary Report on Patentability dated May 24, 2011 for Intl. Pat. App. No. PCT/US09/065764, filed on Nov. 24, 2009, published on May 27, 2010 as WO 10/060094 (Applicant—Kimberly-Clark, Worldwide Inc . . . ).
Intl. Search Report with Written Opinion dated Apr. 28, 2010 for Intl. Pat. App. No. PCT/US09/065764, filed on Nov. 24, 2009, published on May 27, 2010 as WO 10/060094 (Applicant—Kimberly-Clark, Worldwide Inc.).
Reply to Communication from Examining Division filed on Jun. 16, 2011 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division dated Feb. 8, 2011 for EP App. No. 05797894.2, which claims priority to PCT/US05/033600, filed Sep. 19, 2005, published on Mar. 30, 2006 as WO 06/034249 (Applicant—Acrymed, Inc.).
Reply to Communication from Examining Division filed on Jun. 23, 2009 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division dated Dec. 17, 2008 for EP App. No. 05797894.2, which claims priority to PCT/US05/033600, filed Sep. 19, 2005, published on Mar. 30, 2006 as WO 06/034249 (Applicant—Acrymed, Inc.).
Supplemental European Search Report and Opinion dated Oct. 21, 2008 for EP App. No. 05797894.2, which claims priority to PCT/US05/033600, filed Sep. 19, 2005, published on Mar. 30, 2006 as WO 06/034249 (Applicant—Acrymed, Inc.).
Amendments before examination filed on Apr. 18, 2007 for EP App. No. 05797894.2, which claims priority to PCT/US05/033600, filed Sep. 19, 2005, published on Mar. 30, 2006 as WO 06/034249 (Applicant—Acrymed, Inc.).

(56) References Cited

OTHER PUBLICATIONS

Intl. Preliminary Report on Patentability dated May 1, 2007 for Intl. Pat. App. No. PCT/US05/033600, filed Sep. 19, 2005, published Mar. 30, 2006 as WO 06/034249 (Applicant—Acrymed, Inc.).
Intl. Search Report with Written Opinion dated Apr. 18, 2007 for Intl. Pat. App. No. PCT/US05/033600, filed on Sep. 19, 2005, published on Mar. 30, 2006 as WO 06/034249 (Applicant—Acrymed, Inc.).
Final Rejection dated Jun. 13, 2011 for U.S. Appl. No. 11/663,236 filed Mar. 19, 2007 (Karandikar et al.).
Response after Non-Final Action filed on Apr. 12, 2011 for U.S. Appl. No. 11/663,236, filed Mar. 19, 2007 (Karandikar et al.).
Non-Final Rejection dated Dec. 13, 2010 for U.S. Appl. No. 11/663,236, filed Mar. 19, 2007 (Karandikar et al.).
Response to Restriction/Election Requirement filed on Sep. 23, 2010 for U.S. Appl. No. 11/663,236, filed Mar. 19, 2007 (Karandikar et al.).
Restriction/Election Requirement dated Jun. 23, 2010 for U.S. Appl. No. 11/663,236, filed Mar. 19, 2007 (Karandikar et al.).
Preliminary Amendment filed on Mar. 19, 2007 for U.S. Appl. No. 11/663,236, filed Mar. 19, 2007 (Karandikar et al.).
Amendment/Response After Non-Final Action filed on Aug. 9, 2011 for U.S. Appl. No. 09/752,939, filed Dec. 29, 2000 (Inventor—Gibbins).
Non-Final Rejection dated Feb. 15, 2011 for U.S. Appl. No. 09/752,939, filed Dec. 29, 2000 (Inventor—Gibbins).
Amendment Submitted/Entered with CPA/RCE filed on Jan. 18, 2011 for U.S. Appl. No. 09/752,939, filed Dec. 29, 2000 (Inventor—Gibbins).
Notice of Appeal filed on Jun. 17, 2010 for U.S. Appl. No. 09/752,939, filed Dec. 29, 2000 (Inventor—Gibbins).
Final Rejection dated Feb. 25, 2010 for U.S. Appl. No. 09/752,939, filed Dec. 29, 2000 (Inventor—Gibbins).
Amendment/Response After Non-Final Action filed on Dec. 3, 2009 for U.S. Appl. No. 09/752,939, filed Dec. 29, 2000 (Inventor—Gibbins).
Non-Final Rejection dated Jun. 4, 2009 for U.S. Appl. No. 09/752,939, filed Dec. 29, 2000 (Inventor—Gibbins).
Amendment Submitted/Entered with CPA/RCE filed on Mar. 16, 2009 for U.S. Appl. No. 09/752,939, filed Dec. 29, 2000 (Inventor—Gibbins).
Final Rejection dated Sep. 18, 2008 for U.S. Appl. No. 09/752,939, filed Dec. 29, 2000 (Inventor—Gibbins).
Amendment/Response After Non-Final Action filed on Apr. 28, 2008 for U.S. Appl. No. 09/752,939, filed Dec. 29, 2000 (Inventor—Gibbins).
Non-Final Rejection dated Dec. 28, 2007 for U.S. Appl. No. 09/752,939, filed Dec. 29, 2000 (Inventor—Gibbins).
Amendment Submitted/Entered with CPA/RCE filed on Oct. 9, 2007 for U.S. Appl. No. 09/752,939, filed Dec. 29, 2000 (Inventor—Gibbins).
Advisory Action (PTOL-303) dated Sep. 4, 2007 for U.S. Appl. No. 09/752,939, filed Dec. 29, 2000 (Inventor—Gibbins).
Amendment After Final Rejection filed on Aug. 6, 2007 for U.S. Appl. No. 09/752,939, filed Dec. 29, 2000 (Inventor—Gibbins).
Final Rejection dated Jun. 6, 2007 for U.S. Appl. No. 09/752,939, filed Dec. 29, 2000 (Inventor—Gibbins).
Supplemental Response/Amendment filed on Apr. 3, 2007 for U.S. Appl. No. 09/752,939, filed Dec. 29, 2000 (Inventor—Gibbins).
Amendment/Response After Non-Final Action filed on Feb. 14, 2007 for U.S. Appl. No. 09/752,939, filed Dec. 29, 2000 (Inventor—Gibbins).
Examiner Interview Summary Record (PTOL-413) dated Jan. 17, 2007 for U.S. Appl. No. 09/752,939, filed Dec. 29, 2000 (Inventor—Gibbins).
Non-Final Rejection dated Sep. 14, 2006 for U.S. Appl. No. 09/752,939, filed dated Dec. 29, 2000 (Inventor—Gibbins).
Amendment Submitted/Entered with CPA/RCE filed on Aug. 7, 2006 for U.S. Appl. No. 09/752,939, filed Dec. 29, 2000 (Inventor—Gibbins).
Amendment initialed by Examiner/Advisory Action (PTOL-303) dated May 18, 2006 for U.S. Appl. No. 09/752,939, filed Dec. 29, 2000 (Inventor—Gibbins).
Amendment After Final Rejection filed on May 8, 2006 for U.S. Appl. No. 09/752,939, filed Dec. 29, 2000 (Inventor—Gibbins).
Final Rejection dated Mar. 7, 2006 for U.S. Appl. No. 09/752,939, filed Dec. 29, 2000 (Inventor—Gibbins).
Amendment/Response After Non-Final Action filed on Dec. 1, 2005 for U.S. Appl. No. 09/752,939, filed Dec. 29, 2000 (Inventor—Gibbins).
Non-Final Rejection dated Aug. 2, 2005 for U.S. Appl. No. 09/752,939, filed Dec. 29, 2000 (Inventor—Gibbins).
Amendment Submitted/Entered with CPA/RCE filed on Jun. 15, 2005 for U.S. Appl. No. 09/752,939, filed Dec. 29, 2000 (Inventor—Gibbins).
Advisory Action (PTOL-303) dated Jun. 8, 2005 for U.S. Appl. No. 09/752,939, filed Dec. 29, 2000 (Inventor—Gibbins).
Amendment After Final Rejection filed on Mar. 30, 2005 for U.S. Appl. No. 09/752,939, filed Dec. 29, 2000 (Inventor—Gibbins).
Final Rejection dated Dec. 16, 2004 for U.S. Appl. No. 09/752,939, filed Dec. 29, 2000 (Inventor—Gibbins).
Amendment/Response After Non-Final Action filed on Sep. 16, 2004 for U.S. Appl. No. 09/752,939, filed Dec. 29, 2000 (Inventor—Gibbins).
Non-Final Rejection dated May 17, 2004 for U.S. Appl. No. 09/752,939, filed Dec. 29, 2000 (Inventor—Gibbins).
Decision to Withdraw from Issue dated Apr. 26, 2004 for U.S. Appl. No. 09/752,939, filed Dec. 29, 2000 (Inventor—Gibbins).
Notice of Allowance dated Jan. 23, 2003 for U.S. Appl. No. 09/752,939, filed Dec. 29, 2000 (Inventor—Gibbins).
Amendment Submitted/Entered with CPA/RCE filed on Nov. 15, 2002 for U.S. Appl. No. 09/752,939, filed Dec. 29, 2000 (Inventor—Gibbins).
Advisory Action (PTOL-303) dated Nov. 19, 2002 for U.S. Appl. No. 09/752,939, filed Dec. 29, 2000 (Inventor—Gibbins).
Amendment After Final Rejection filed on Oct. 15, 2002 for U.S. Appl. No. 09/752,939, filed Dec. 29, 2000 (Inventor—Gibbins).
Final Rejection dated Jul. 15, 2002 for U.S. Appl. No. 09/752,939, filed Dec. 29, 2000 (Inventor—Gibbins).
Amendment/Response After Non-Final Action filed on Apr. 18, 2002 for U.S. Appl. No. 09/752,939, filed Dec. 29, 2000 (Inventor—Gibbins).
Examiner Interview Summary Record (PTOL-413) dated Apr. 11, 2002 for U.S. Appl. No. 09/752,939, filed Dec. 29, 2000 (Inventor—Gibbins).
Non-Final Rejection dated Dec. 18, 2001 for for U.S. Appl. No. 09/752,939, filed Dec. 29, 2000 (Inventor—Gibbins).
Deitch, E., et al, Sliver-Nylon: a New Antimicrobial Agent; Antimicrobial Agents and Chemotherapy, Mar. 1983, p. 356-359 vol. 23, No. 3.
Deitch, E., et al., Abstract, Silver-impregnated nylon cloth dressing: in vitro and in vivo evaluation of antimicrobial activity, J. Trauma, 1987, p. 301-304, vol. 27, No. 3.
MacKeen, P., et al., Silver-Coated Nylon Fiber as an Antibacterial Agent, Antimicrobial Agents and Chemotherapy, Jan. 1987, p. 93-99, vol. 31, No. 1.
Acticoat RTM, Silver Coated Dressing, The Westaim Corporation, 1988.
Liz-Marzán et al., "Reduction and Stabilization of Silver Nanoparticles in Ethanol by Nonionic Surfactants," *Langmuir*, vol. 12, 1996, pp. 3585-3589.
Pastoriza-Santos et al., "Reduction of silver nanoparticles in DMF. Formation of monolayers and stable colloids," *Pure Appl. Chem.*, vol. 72, Nos. 1-2, 2000, pp. 83-90.
Article—Wagner et al, "Characterization of Silver Anthranilate, a Promising Antibacterial Agent," *Acta Farm. Bonaerense*, vol. 21, No. 1, 2002, pp. 27-30.
Supplementary European Search Report dated Dec. 29, 2011, 8 pages.

\* cited by examiner

ANTIMICROBIAL DEVICES AND COMPOSITIONS

RELATED APPLICATIONS

This application is a 35 USC § 371 national stage application of PCT Patent Application No. PCT/US2005/027260, filed Aug. 1, 2005, which claims the priority of U.S. Provisional Patent Application No. 60/592,535, filed Jul. 30, 2004, each of which is incorporated in its entirety.

FIELD OF THE INVENTION

The invention pertains to antimicrobial devices and compositions comprising metal compounds, such as silver. In particular, the methods and devices can be used in applications where an antimicrobial environment is useful.

BACKGROUND OF THE INVENTION

Silver is known to possess broad spectrum antimicrobial activity and has been incorporated in a variety of medical care products such as dressings, hydrogels, hydrocolloids, foams, creams, gels, lotions, catheters, sutures, bandages, and positioning devices. Though specifically not recognized, the antimicrobial properties of silver were known and exploited since the times of ancient Mediterranean and Asiatic cultures. References have been made to the use of silver vessels to prevent spoilage of water during storage and of silver foil or plates in the treatment of wounds and bone fractures.

Von Nageli first systematically studied the lethal effects of metals, including silver, on bacteria and other life forms and coined the term "oligodynamic effect" for the phenomenon (C. Von Nageli, Denkschriften der Schweiz Naturforsch. Ges., Vol. 33, pp 1 (1893)). Generally speaking, the oligodynamic effect is limited to solutions in which metal ion concentration is several orders of magnitude below that which would be harmful to the patient's tissue. In the case of silver, this value is about $10^{-6}$ to $10^{-9}$ molar.

A silver compound that can maintain a silver ion concentration of at least $10^{-9}$ molar can function as antimicrobial agent. The majority of known silver salts are sparingly soluble, i.e., possess very low solubility product $K_{sp}$, and thus, the silver ion concentration in solutions are generally very low. An exception is silver nitrate, which is completely ionized at all concentrations but is prone to the loss of silver ions by de-activation by surfaces contacting the solution. Despite the slow dissolution in water due to low solubility of silver salts, not all silver compounds are useful as antimicrobial agents because of silver's adverse properties. These include a short half-life, the rapid inactivation of silver by protein or compounds having thiol groups, and light- or heat-mediated discoloration.

The antimicrobial activity and action of silver was reviewed in Russell and Hugo (Prog. Medicinal Chemistry, Vol. 31, pp 351 (1994)). It is believed that the lethal activity of silver towards microbes is due to silver's multi-site attack on microbial cells. Silver ions possess high affinity for thiol, amino and carboxyl groups and oligonucleotide bases and bind irreversibly to these groups, disrupting cells normal growth cycles and killing them. Because of silver's ability to target multiple sites on cells, the risk of microbes developing resistance to silver is extremely unlikely. Therefore, silver has found widespread use as a germicidal agent. With the emergence of methicillin-resistant *Staphylococcus aureus* and vancomycin-resistant *Enterococcus faecium* in recent years, the focus has increasingly shifted to the use of silver as a more robust and reliable antimicrobial agent.

Many silver compounds have been found to be useful. Silver nitrate has been used in eye drops to treat neonatal eye infections. In stick form, silver nitrate has been used to treat warts and in lotions to treat lesions. Silver nitrate combined with ammonia has been used as a antimicrobial dental protective. Several other silver salts such as acetate, citrate, lactate, picrate and methylene bis naphthalene sulfonate have found use in different therapeutic compositions—eye lotions, dust powder for wounds, in astringents and antiseptic, in treating vaginal trichomonoiasis and candidiasis and in treating burns, varicose ulcers and pressure sores. Silver protein complexes have also been widely used in preparations such as creams, lotions and ointments. In creams and lotions, a sulfonamide derivative, silver sulphadiazine, has been successful in the treatment of burns and acute and chronic wounds. However, there have been reports of microbes in hospital settings developing resistance to sulphadiazine thus limiting its widespread use.

Medical devices containing silver must meet the same requirements as other antimicrobial medical devices to be commercially successful. Silver-containing devices must maintain the same aesthetic appearance and feel and provide antimicrobial function for prolonged periods. Unfortunately, most currently available devices incorporating silver compounds are only able to fulfill the requirements to some degree, i.e. they are able to provide antimicrobial effect on sustained basis but they discolor over time. A few devices are able to fulfill both requirements but are not biocompatible at effective concentrations.

Silver-containing medical devices are prone to light and heat-induced discoloration. Often these products in contacting body parts or skin cause undesirable staining. At worst, repeated staining can lead to permanent discoloration, a condition known as argyria. The light and thermal instability of these products may also cause reliability problems in the manufacture and shelf life storage. Efforts have been tried to overcome these problems, but they have been unsuccessful, due to toxicity, continued light sensitivity or other issues.

While various approaches may be somewhat successful in imparting light stability to some products, most approaches are not broadly applicable. Silver compounds that possess good light stability do not necessarily have good thermal stability, which is often useful because in manufacturing, drying steps or sterilization operations may involve high temperatures.

None of the current silver stabilization procedures are practical to implement in preparing medical devices, such as traditional dressings, with antimicrobial property such as cotton or polyester blended cotton gauzes or sponges, or other devices. For example, in treating a cotton gauze, moderate amount of salts (chlorides) may be tolerated but excess salts tend to make a gauze material stiff giving it a crispy feel. However, with only moderate amount of salts, the light protective action may not be as effective. Occlusion by polyethylene glycols may not appropriate as it could be expensive and the presence of copper salts stain the gauze yellow. In the alternative, cotton gauzes can be rendered antimicrobial with antibiotics or other chemical agents (biguanides and chlorohexidine derivatives) but they don't perform as well.

Therefore, there is a need for antimicrobial products, including traditional dressings, such as gauze products, that provide antimicrobial characteristics from the presence of silver and provide sustained release but do not discolor under light, heat and sterilization conditions, and which are relatively inexpensive and straightforward to manufacture.

SUMMARY

The present invention comprises methods and compositions comprising metals, such as zinc, copper and silver. In particular, the metal, such as silver, zinc or copper, is found in association with an anion or in a complex, referred to herein as a ligand, where the ratio of the metal to a ligand is less than 1 to 1 (i.e., Metal(Ag):Ligand where Ligand≥Metal(Ag) on a molarity basis. For brevity sake, compounds disclosed herein are referred to as silver compounds, but it is to be understood that silver, copper or zinc compounds are contemplated by the disclosed compounds, compositions and devices. Silver compounds contemplated by the present invention are disclosed herein. The silver compounds taught herein are may be used in antimicrobial compositions and devices, including, but not limited to, medical products such as wound care products or patient care products. Particular compounds include metal salts of copper, zinc and silver of saccharin derivatives wherein the substituent on imide nitrogen is hydrogen, silver complex compounds such as silver benzodiazepines complexes and benzodiazepine derivatives, and polymeric silver compounds are also contemplated by the present invention.

Methods of using the compounds as antimicrobial agents in compositions and in treating surfaces and medical devices and in wound care products are taught herein as are methods of making and using the antimicrobial compositions and devices.

The antimicrobial devices of the present invention resist discoloration induced by light or thermal exposure. The silver compounds of the present invention are generally sparingly soluble in water and this low solubility and inertness to light and heat allows the devices incorporating such compositions to maintain antimicrobial activity over long periods of time and yet not discolor. The ability to resist discoloration by light or heat distinguishes the present invention from prior silver-based antimicrobial agents. The stability of the silver compounds of the present invention against heat and light precludes the need for stabilization chemistry and saves costs in the preparation of antimicrobial compositions and devices.

DETAILED DESCRIPTION OF THE INVENTION

The present invention comprises methods and compositions for making and using antimicrobial devices and compositions comprising metallic compounds. The antimicrobial character of the devices and compositions is provided by metals, including silver, copper and zinc. The compositions and devices of the present invention are useful because they are resistant to discoloration by exposure to heat or light and do not stain skin, tissues or other surfaces which they contact.

Methods for making many of the metal compounds of the present invention are known to those skilled in the art or may be derived using chemical techniques. In general, the silver compounds of the present invention may be prepared by mixing stoichiometric amounts of solutions of a silver salt such as silver nitrate or acetate with a corresponding alkali or alkaline earth metal salt of an organic anionic compound. Slight excess over stoichiometry of alkali or alkali earth metal compounds is also contemplated by the invention. Solutions of soluble silver salts can be mixed with corresponding organic compounds directly rather than in their alkali or alkaline earth metal salts, and especially those organic compounds that are acidic —NH compounds. When preparing silver compounds dispersed on carrier supports, the mixing step may be carried out in the presence of insoluble carrier materials.

Silver compounds of the present invention can be admixed or combined into many different compositions to render such compositions antimicrobial. Such compositions include, but are not limited to, suspensions, lotions and creams, ointments, jellies, gels, pessaries, compositions based on inorganic carriers such as porous glasses, oxides, silicates, talc, mica, silica, titania, zirconia, insoluble polymeric microspheres, hydroxy apatite, cellulose powder, chitin, chitosan, and cross-linked polymers. For example, a composition may comprise a fine suspension of a silver compound with or without surfactant, dispersant or stabilizing agent. In another example, the composition may be a topical gel that provides moisturizing, soothing and bioburden reducing action over long periods of time and be minimally or completely non-staining.

Compositions of the present invention may comprise one or more silver compounds, or may comprise one or more active agents, such as other antibiotics. For example, in addition to the silver compounds taught herein, other active agents such as antibiotics or silver compounds already known in the prior art can also be included in the antimicrobial compositions. Other active agents include, but are not limited to, antimicrobial agents, antifungal agents, antiviral agents, growth factors, angiogenic factors, anaesthetics, mucopolysaccharides and wound healing proteins. The compositions may further comprise additives such as fragrances, colorants, emollients, surfactants, dispersants, moisturizers, viscosity modifiers, acids and bases for adjusting pH, gelling agents, opacifiers, fillers, humectants, polymers, oligomers, waxes, mineral oils, petrolatum bases or other ingredients, excipients, diluents or needed components to improve or impart specific formulation properties. Additives, such as those known to be used in formulations, may be used in the compositions with the proviso that their inclusion should have minimal effect on the compositions with respect to discoloration by light or heat and that the antimicrobial property may not be affected adversely during the preparation, storage and use. Those skilled in the art will recognize silver stabilized compositions comprising silver compounds of the present invention can be formulated with an ordinary amount of experimentation.

Compositions of the present invention may comprise carriers or supports which are useful for increasing the bulk of a composition. Carriers or supports may be used for used for finely dispersing the silver compounds of the present invention and are generally physiologically inert and stable in an aqueous environment. Suitable carriers or supports materials include oxides of titanium, magnesium, aluminium, silicon, cerium, zirconium, hafnium, niobium, tantalum, calcium hydroxyapatite and barium sulphate. The list presented here is for illustration and by no means limiting or exhaustive.

Compositions of the present invention may be used in the treatment of disruptions of the integumentary system, the skin, coverings of organs, mucous membranes, and other coverings of body surfaces, including, but not limited to, wounds, diabetic ulcers, burns, burn wounds and ulcers, skin lesions, and infections of skin and mucous membranes. Compositions and devices of the present invention may be used on living and nonliving surfaces to provide an antimicrobial environment, and may be used for humans, animals and plants.

Antimicrobial compositions and devices with varying durations of antimicrobial activity are provided by the present invention. The activity may last from a few hours to several days. When included in antimicrobial compositions, the amount of silver compounds is dictated by several factors. If long term application is contemplated then the amount of silver compounds is increased to a level that will provide an effective amount of silver on the last day of the expected duration of use. However, the amount of silver compounds cannot be increased arbitrarily so as to exceed a level that will cause cytoxicity to the mammalian cells. Antimicrobial compositions incorporating therapeutically effective amounts of silver compounds without causing undesirable cytotoxicity and unwanted discoloration or staining are contemplated by the present invention.

The present invention comprises antimicrobial medical devices and wound care products comprising silver compounds, uses and methods of preparation of such devices and products. Light and heat stable silver compounds are combined with medical and wound care devices to render such medical and wound care devices antimicrobial, while maintaining light and heat stability. Examples of medical devices rendered antimicrobial using the silver compounds of the present invention include, but are not limited to, dry or wet matrices, hydrophobic or hydrophilic matrices such as cellulose ether derivatives, hydroxyl alkyl cellulose ether derivatives, hydroxyl alkyl cellulose derivatives or mixtures thereof, cotton, rayon, acrylics, acetate fibers, alginates and other synthetic and natural polymers and their blends, hydrocolloid dressings, dressings used in wet therapy, super-absorbent foams, hydrophilic polyurethane foams, activated charcoal dressings, compresses, xeroform petrolatum dressings, venous, urinary and pain management system catheters, stents, guidewires, shunts, cannulae, catheter adapters and other solid and hollow tubular devices, sutures, incontinence pads, ostomy pouches and plugs, haemostats, urine collection bags, and other waste collection containers.

Additionally, by use of the antimicrobial compositions of the present invention, many devices and compositions that have properties other than being antimicrobial or providing an antimicrobial environment may be rendered antimicrobial. For example, addition of the antimicrobial compositions of the present invention to paints or inks will render them resistant to microbial growth and odor without hindering their applications as paints or inks. Silver compounds and compositions of the present invention may also be used in other devices and compositions for the control of odor or microbial growth, or other unwanted microbial by-products from wound exudates, in dental compositions, in products used in bowel or vascular surgery, oral hygiene products, bathroom products, textile products, coatings, natural or synthetic polymers adhesives, paint products, polymer films, paper, leather, rubber and plastic articles. Unfinished and finished articles such as yarns, threads, or bolts of cloth or carpets may also be rendered antimicrobial.

Compounds of the Present Invention

The present invention comprises use of metal compounds, including silver, zinc and copper. For ease of reference, silver will be used herein, but it is to be understood that any one of the three metals is intended. Compounds of the present invention include, but are not limited to, silver diazepine complexes, polymeric silver compounds, heavy metal compounds of saccharin, such as silver compounds of saccharin, as antimicrobial agents in compositions and medical devices and products. Medical devices and compositions of the present invention comprise silver compounds taught herein including, but not limited to, silver thiocyanate, silver oxide, silver sulfate, silver chloride, silver bromide, silver iodide, silver alkyl carboxylate (C1 to C12), silver aryl sulfonate (C1 to C4 alkyl phenyl), silver carbonate, silver sulfide, silver phosphoranilide, silver phosphate, silver hydroxide, silver hyaluronate, silver benzoate, silver tartarate, silver thiosulfate complex, silver laurate, silver zeolite, silver zirconium phosphate, silver alginate, silver ascorbate, silver folate, silver gluconate, silver salicylate, silver para amino benzoate, silver para amino salicylate, silver acetyl salicylate, silver EDTA, silver laurate, silver zeolite, silver zirconium phosphate, silver alginate, silver ascorbate, silver folate, silver iodate, silver oxalate, silver palmitate, silver perborate, silver stearate, silver succinate, silver thioglycolate, silver hydantoin complex, silver barbiturate, silver allantoinate, silver amine complexes (primary amine, tetiary amine), silver salicylate, silver para amino benzoate, silver para amino salicylate, silver acetyl salicylate, silver EDTA, silver gluconate In one embodiment of the invention, antimicrobial compounds comprise compounds of silver as represented by:

$M^+X_{(n)}$ wherein,

M is silver, zinc or copper n is 1 or more

X is selected from A, B or C where $R_1$ and $R_2$ are —P or —WP; and

W is a linker of branched alkyl chain of 1-27 carbon atoms, straight alkyl chain of 1-27 carbon atoms, monoethers containing 2-20 carbon atoms and polyethers containing 2-20 carbon atoms; and P is hydrogen, halogen atoms, haloalkyl, amide, sulfate, phosphate, quarternary ammonium, hydroxyl, hydroxymethyl, phosphonate, amino, carboxyl, carboxymethyl, carbonyl, acetyl, succinimidyl ester, isothiocyanate, isocyanate, iodoacetamide, maleimide, sulfonyl halide, phosphoramidite, alkylimidate, arylimidate, acide halide, substituted hydrazines, substituted hydroxylamines, carbodiimides, cyano, nitro, fluormethyl, nitrophenyl, sulfonamide, alkenyl or alkynyl;

and $R_3$ and $R_4$ are hydrogen, straight alkyl with $C_1$-$C_8$ carbon atoms, optionally terminating in aryl or substituted aryl groups, branched alkyl with $C_1$-$C_8$ carbon atoms, phenyl, substituted phenyl, benzyl, substituted benzyl and fluoromethyl; and A is one of the following:

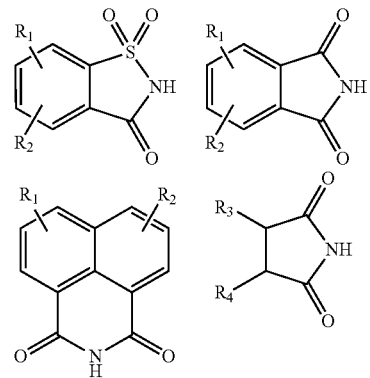

-continued

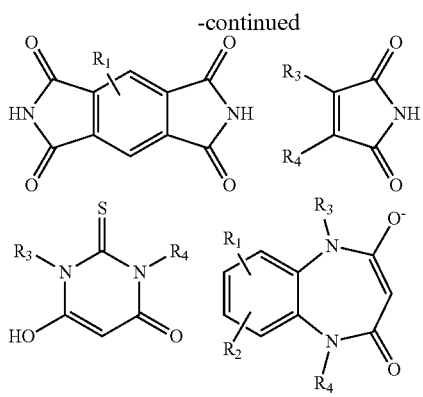

and

B is one of the following

R₁ and R₂ are —P and —WP as described above, and W is a linker as described above, and R₃ and R₄ are as described above.

C is behenate or bis(2-ethylhexyl)sulfosuccinate

Another embodiment of the invention comprises complexes of silver $M^+[Y^-]_n$ where M is silver, zinc or copper; n is 1 or more; and Y is the following:

where R₁ and R₂ are selected from the group consisting of —P and —WP; as described above, and W is a linker as described above. R₃ and R₄ are described above and Z is C6 or C8 alkyl.

Another embodiment of the present invention comprises the following where $M^+[Y'^-]n$ where M is silver, copper or zinc n is 1 or more and Y'— is the following:

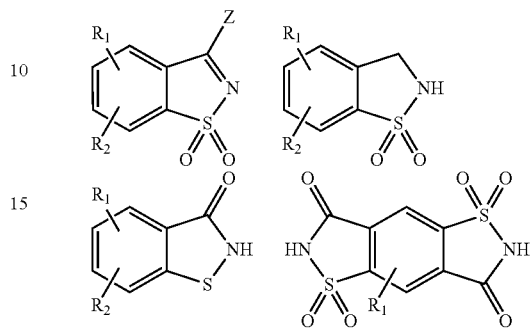

where

R₁ and R₂ are selected from the group consisting of —P and —WP; as described above, and W is a linker as described above. R₃ and R₄ are described above and Z is amino, alkylamino, chloro, or HNX, wherein X in HNX comprises aryl, hydroxyl, amino, NHC₆H₅, or NHCONH₂. Other ligands that form silver compounds of the present invention comprise the following shown in Table 1:

TABLE 1

| ID | Name | Structure |
|---|---|---|
| 1.01 | 1,1-Dioxo-1,2-dihydro-1λ⁶-benzo[α]isothiazol-3-one | 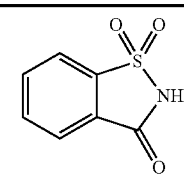 |
| 1.02 | Pyrrolo[3,4-f]isoindole-1,3,5,7-tetraone | 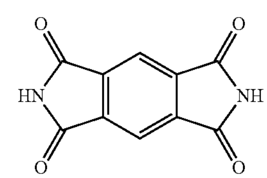 [SMILES: O=c1[nH]c(=O)c2cc3c(=O)[nH]c(=O)c3cc12] |
| 1.03 | Aziridine | 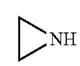 |
| 1.04 | Azetidine | 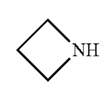 |
| 1.05 | Isoindole-1,3-dione | 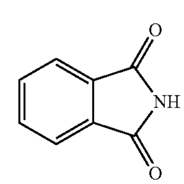 [SMILES: O=C1NC(=O)c2ccccc21] |
| 1.06 | Pyrimidine 2,4,6-trione | 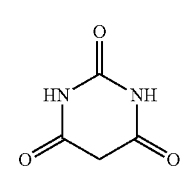 |

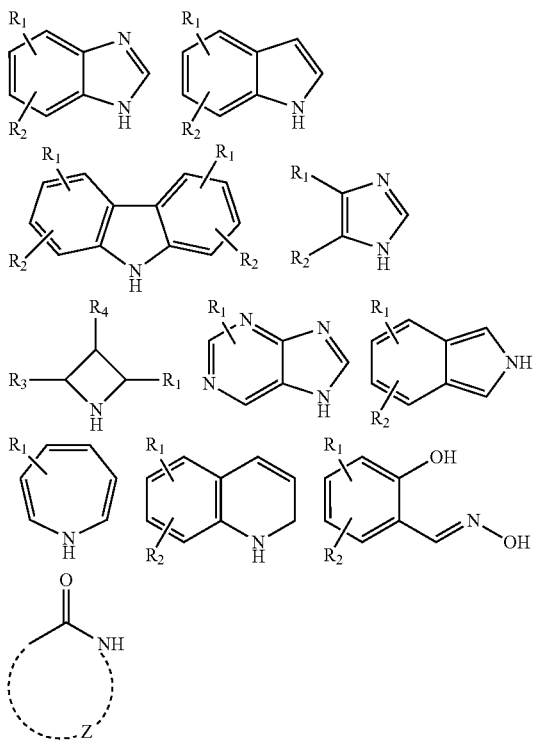

TABLE 1-continued

| ID | Name | Structure |
|---|---|---|
| 1.07 | 2-Thioxo-dihydro-pyrimidine-4,6-dione | 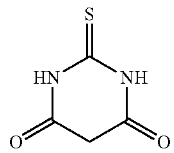 |
| 1.08 | Pyrrole-2,5-dione | 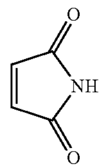 |
| 1.09 | Imidazole-2,4-dione | 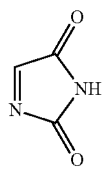 |
| 1.10 | Benzo[de]iso-quinoline-1,3-dione | 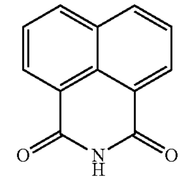 [SMILES: O=C1NC(=O)c2cccc3cccc1c23] |

Polymer, where $x+y=1$, and x is between 0 and 0.5 and x and y are weight fractions with molecular weights between 5000 and 100,000 Daltons.

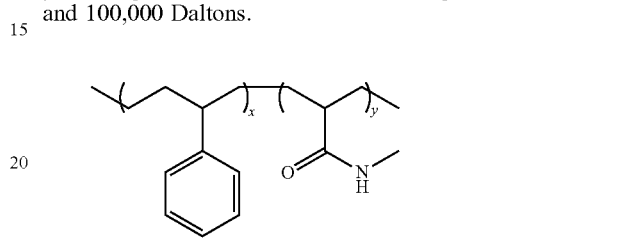

Another disclosed embodiment of the invention comprises polymeric silver compounds of the following, where $x+y=1$ and x is between 0 and 0.5; $m+n=1$ and m is between 0 and 0.5; and x, y, m and n are weight fractions and have molecular weights between 5000 and 100,000 Daltons.

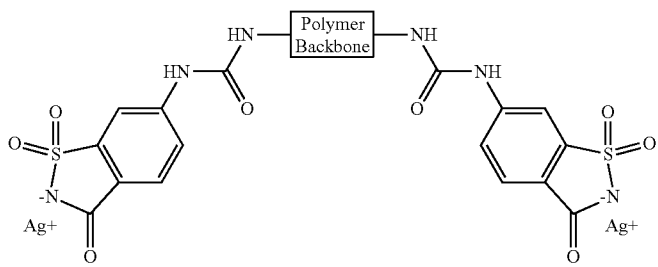

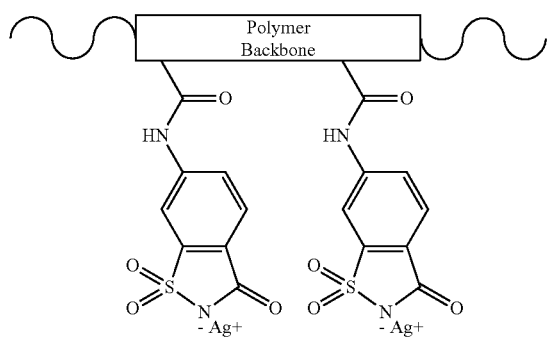

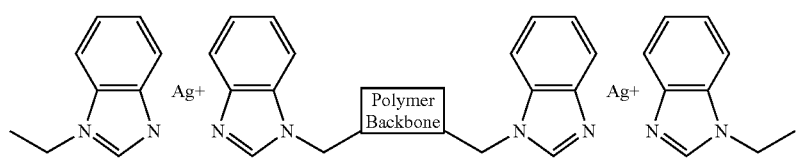

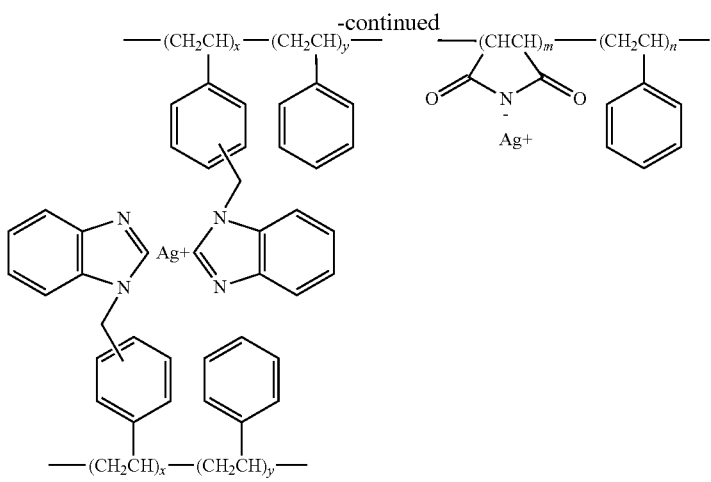

Other silver compounds of the present invention are shown in Table 2.

TABLE 2

| ID | Name | Structure |
|---|---|---|
| 2.01 | Silver 5-chlorosalicylaldoxime | 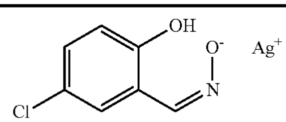 |
| 2.02 | Silver saccharin | 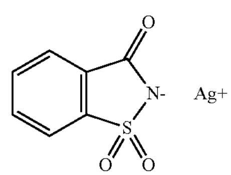 |
| 2.03 | Silver 5-nitrosalicylaldoxime | 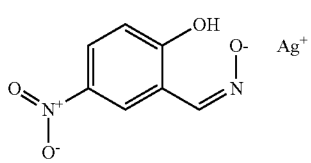 |

Silver compounds for incorporation into compositions or devices of the present invention wherein the compound is X+Y−, wherein X is silver and Y is acesulfame, or derivatives thereof.

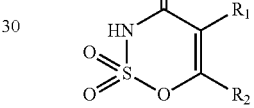

$R_1$ and $R_2$ are a hydrogen atom, optionally a branched alkyl group having from one to 20, or up to 10 carbon atoms, an aromatic hydrocarbon radical having up to 10 carbon atoms, or an aliphatic acyl radical having from two to four carbon atoms, $R_2$ is an optionally branched alkyl group having up to 20 carbon atoms, or up to 10 carbon atoms, or an aromatic hydrocarbon radical having up to 10 carbon atoms, and in which $R_1$ and $R_2$ may also be linked to form an isocyclic ring which optionally may be substituted by further hydrocarbon radicals. Also included are the salts of the compounds of this formula. Additional compounds are shown in Table 3.

TABLE 3

| ID | Name | Structure |
|---|---|---|
| 3.01 | 3,4-dihydro-6-methyl-1,2,3-oxathiazin-4-one-2,2-dioxide | 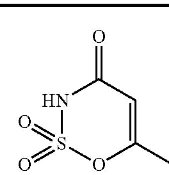 |
| 3.02 | 3,4-dihydro-6-n-butyl-1,2,3-oxathiazin-4-one-2,2-dioxide | 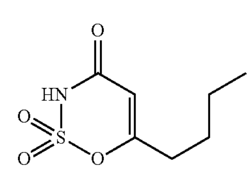 |

TABLE 3-continued

| ID | Name | Structure |
|---|---|---|
| 3.03 | 3,4-dihydro-6-phenyl-1,2,3-oxathiazin-4-one-2,2-dioxide | 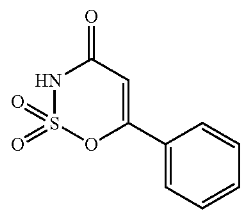 [SMILES: O=C1C=C(c2ccccc2)OS(=O)(=O)N1] |
| 3.04 | 3,4-dihydro-5,6-dimethyl-1,2,3-oxathiazin-4-one-2,2-dioxide | 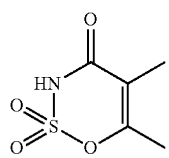 |
| 3.05 | 3,4-dihydro-5-methyl-6-ethyl-1,2,3-oxathiazin-4-one-2,2-dioxide | 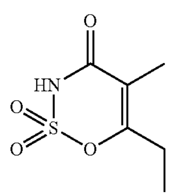 |
| 3.06 | 3,4-dihydro-5-methyl-6-phenyl-1,2,3-oxathiazin-4-one-2,2-dioxide | 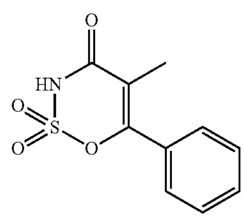 [SMILES: CC1=C(c2ccccc2)OS(=O)(=O)NC1=O] |
| 3.07 | 3,4-dihydro-5-ethyl-6-methyl-1,2,3-oxathiazin-4-one-2,2-dioxide | 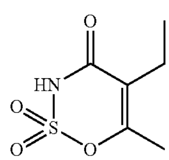 |
| 3.08 | 3,4-dihydro-5-n-propyl-6-methyl-1,2,3-oxathiazin-4-one-2,2-dioxide | 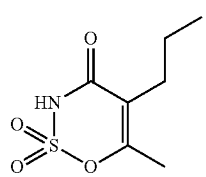 |
| 3.09 | 3,4-dihydro-5-isopropyl-6-methyl-1,2,3-oxathiazin-4-one-2,2-dioxide | 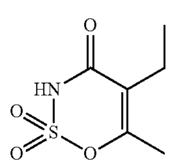 |
| 3.10 | 3,4-dihydro-5-n-octyl-6-methyl-1,2,3-oxathiazin-4-one-2,2-dioxide | 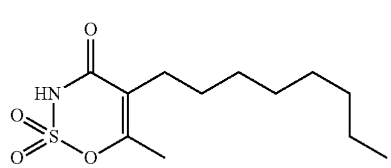 [SMILES: CCCCCCCCC1=C(C)OS(=O)(=O)NC1=O] |

TABLE 3-continued

| ID | Name | Structure |
|---|---|---|
| 3.11 | 3,4-dihydro-5-phenyl-6-methyl-1,2,3-oxathiazin-4-one-2,2-dioxide | 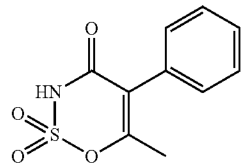 [SMILES: CC1=C(c2ccccc2)C(=O)NS(=O)(=O)O1] |
| 3.12 | 3,4-dihydro-5-ethyl-6-n-propyl-1,2,3-oxathiazin-4-one-2,2-dioxide | 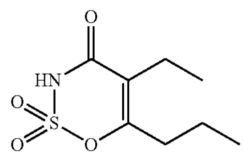 |
| 3.13 | 3,4-dihydro-5-n-propyl-6-n-butyl-1,2,3-oxathiazin-4-one-2,2-dioxide | 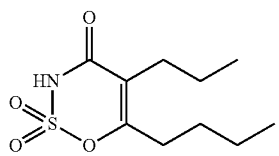 [SMILES: CCCCC1=C(CCC)C(=O)NS(=O)(=O)O1] |
| 3.14 | 3,4-dihydro-5-n-butyl-6-n-amyl-1,2,3-oxathiazin-4-one-2,2-dioxide | 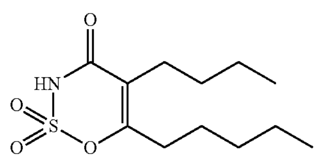 [SMILES: CCCCCC1=C(CCCC)C(=O)NS(=O)(=O)O1] |
| 3.15 | 3,4-dihydro-5,6-tetramethylene-1,2,3-oxathiazin-4-one-2,2-dioxide | 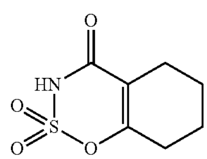 [SMILES: O=C1NS(=O)(=O)OC2=C1CCCC2] |
| 3.16 | 3,4-dihydro-5,6-[2,1-(3,4-dihydro-)naptho]-1,2,3-oxathiazin-4-one-2,2-dioxide | 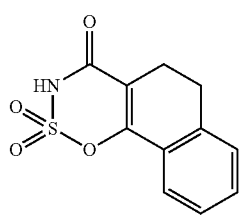 [SMILES: O=C1NS(=O)(=O)OC2=C1CCc1ccccc12] |

Silver compounds for incorporation into compositions or devices of the present invention wherein the compound is silver salts include, for example, the silver salts of benzotriazole or saccharin or, particularly, the silver salts of long chain fatty acids which contain up to 30 carbon atoms, for example silver stearate, silver palmitate, or silver behenate, and include fatty acids with C=10 to 30. Also included are dicarboxylic acids that are long chain, and compounds provided in Table 4.

TABLE 4

| ID | Name | Structure |
|---|---|---|
| 4.01 | Silver behenate | $CH_3(CH_2)_{20}$—C(=O)—O- $Ag^+$ |
| 4.02 | Silver archidate | $CH_3(CH_2)_{18}$—C(=O)—O- $Ag^+$ |
| 4.03 | Silver stearate | $CH_3(CH_2)_{16}$—C(=O)—O- $Ag^+$ |
| 4.04 | Silver palmitate | $CH_3(CH_2)_{14}$—C(=O)—O- $Ag^+$ |
| 4.05 | Silver myristate | $CH_3(CH_2)_{12}$—C(=O)—O- $Ag^+$ |

TABLE 4-continued

| ID | Name | Structure |
|---|---|---|
| 4.06 | Silver laurate | CH$_3$(CH$_2$)$_{10}$COO$^-$ Ag$^+$ |
| 4.07 | Silver sebacate | $^+$Ag $^-$OOC(CH$_2$)$_8$COO$^-$ Ag$^+$ |
| 4.08 | Silver azelate | $^+$Ag $^-$OOC(CH$_2$)$_7$COO$^-$ Ag$^+$ |
| 4.09 | Silver suberate | $^+$Ag $^-$OOC(CH$_2$)$_6$COO$^-$ Ag$^+$ |
| 4.10 | Silver adipate | $^+$Ag $^-$OOC(CH$_2$)$_4$COO$^-$ Ag$^+$ |
| 4.11 | Silver succinate | $^+$Ag $^-$OOC(CH$_2$)$_2$COO$^-$ Ag$^+$ |
| 4.12 | Silver malate | Ag$^+$ $^-$OOC-CH(OH)-CH$_2$-COO$^-$ Ag$^+$ |

Silver long chain fatty acids wherein n is 16-22, comprising the structure below:

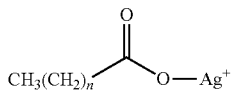

Silver dicarboxylic acids wherein n is 2-12, comprising the structure below:

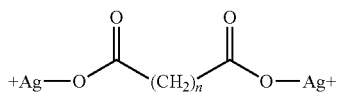

Additional compounds include:
Silver 1-benzotriazoyl:

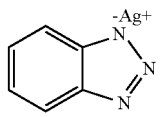

Compounds of the present invention that are silver complexes include the compounds shown in Table 5:

TABLE 5

| ID | Name | Structure |
|---|---|---|
| 5.01 | Thiourea | H$_2$N-C(=S)-NH$_2$ |
| 5.02 | 4-Methoxy-benzenesulfonic acid | CH$_3$O-C$_6$H$_4$-SO$_2$OH |
| 5.03 | 4-Ethylsulfanyl-benzenesulfonic acid | CH$_3$CH$_2$-S-C$_6$H$_4$-SO$_2$OH |
| 5.04 | 4-Phenylsulfanyl-benzenesulfonic acid | C$_6$H$_5$-S-C$_6$H$_4$-SO$_2$OH |
| 5.05 | 2-Aminoethyl methyl sulfide | CH$_3$-S-CH$_2$CH$_2$-NH$_2$ |

TABLE 5-continued

| ID | Name | Structure |
|---|---|---|
| 5.06 | 4-Phenylselanyl-benzenesulfonic acid | 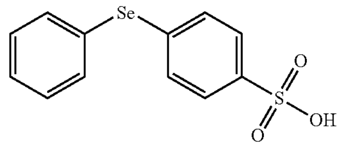 [SMILES: O=S(=O)(O)c1ccc([Se]c2ccccc2)cc1] |
| 5.07 | 3-Amino-benzenesulfonic acid | 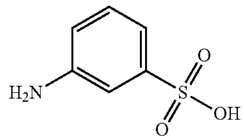 [SMILES: Nc1cccc(S(=O)(=O)O)c1] |
| 5.08 | 2-Diphenylphosphanyl-benzenesulfonic acid | 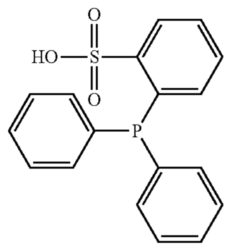 [SMILES: O=S(=O)(O)c1ccccc1P(c1ccccc1)c1ccccc1] |
| 5.10 | Imidazole | 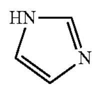 |
| 5.11 | 2,4-Dimethylimidazole | 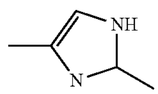 |
| 5.12 | Pyridine | 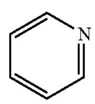 |
| 5.13 | 2-Methylpyridine | 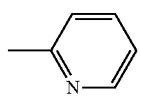 |
| 5.14 | 2,4-Dimethylpyridine | 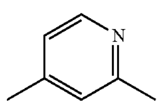 |
| 5.15 | Ammonia | $NH_3$ |
| 5.16 | Ethyl amine | 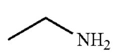 |
| 5.17 | 2-Aminoethanol | 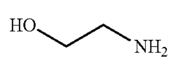 |
| 5.18 | 2-Aminoethyl phosphate | 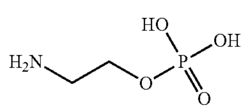 |
| 5.19 | 2-Aminoethyl sulfate | 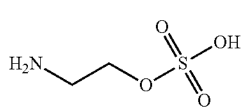 |

The present invention comprises saccharincarboxylic acids and saccharincarboxylic acid esters of the formula:

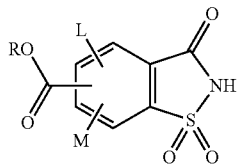

(I)

wherein the substituents have the following meanings: L and M are hydrogen, alkyl, alkoxy, cyano, alkylsulfonyl, nitro, trifluoromethyl and chlorine; and, R is H or alkyl with 1-6 carbon atoms. The present invention further relates to derivatives of saccharin of the formula:

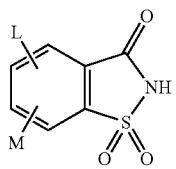

(II)

wherein the L and M are independently selected from hydrogen, alkyl, alkoxy, cyano, alkylsulfonyl, nitro, trifluoromethyl and chlorine.

The present invention also relates to derivatives of saccharin of the formula:

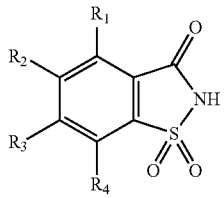

(III)

wherein $R_1$, $R_2$, $R_3$ and $R_4$ are independently selected from hydrogen, alkyl, alkoxy, cyano, alkylsulfonyl, nitro, trifluoromethyl and chlorine.

A stable source of metal for antimicrobial devices is a stable metal-organic complex of (a) a metal suitable for antimicrobial devices with (b) a thioamide according to the present invention is represented by the following formula:

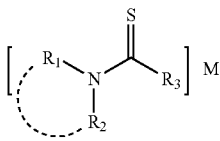

(IV)

wherein M is a metal suitable for antimicrobial devices, such as silver, copper, and the like; $R_1$ and $R_2$ are the same or different and each is hydrogen, alkyl, alkylene, acy, or aryl; $R_3$ is alkyl, —S—$R_4$, or —O—$R_4$, or

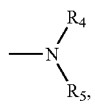

wherein $R_4$ and $R_5$ are hydrogen, alkyl, alkylene, acyl or aryl; and corresponding tautomeric compounds, such as wherein $R_1$ is hydrogen:

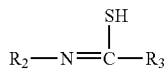

any two R groups can, but need not, be joined to form a heterocyclic ring as represented by the broken lines in structure I.

Alkyl suitably contains one to about 20 carbon atoms, typically one to five carbon atoms, such as methyl, ethyl, propyl butyl, pentyl, decyl and eicosyl. Alkylene suitably contains one to about five carbon atoms, such as methylene, ethylene, propylene, butylene and pentylene. Acyl can be:

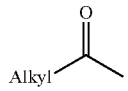

wherein alkyl is as described, especially alkyl containing one to five carbon atoms.

Aryl suitably contains six to about 30 carbon atoms, such as phenyl, tolyl, xylyl and naphthyl. The described alkyl, alkylene, acyl and aryl can contain various substituent groups which do not adversely affect the stability and availability of metal for antimicrobial devices of the described complexes and compounds. Suitable substituent groups include for example, carboxyl, hydroxyl and sulfonic acid groups. Such groups can provide advantages in cases in which it is desirable that the described compound have increased solubility in aqueous compositions and/or increased compatibility with, for example, a binder, if one is used.

Examples of metal-thioamide complexes within Formula I which are stable sources of silver, copper, or zinc for antimicrobial devices are stable silver, copper or zinc complexes of the following compounds: 2-thiobarbituric acid, 1,3-diethyl-2-thiobarbituric acid, 2-thiouracil, imidazolidine-2-thione, 1,3-bis(4-carboxyphenyl)-1,3-dimethylthiourea, 1,3-bis(2-carboxyethyl)-benzimidazole-2-thione, or 4-(3-Methyl-2-thioxo-butyl)-benzoic acid:

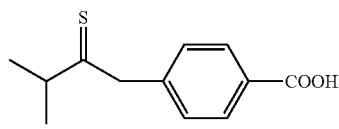

2-Phenyl-4-thioxo-1,4-dihydro-pyrimidine-5-carboxylic acid:

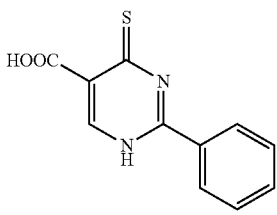 [SMILES: O=C(O)c1c[nH]c(-c2ccccc2)nc1=S]

1-Methyl-2-phenyl-4-thioxo-1,4-dihydro-pyrimidine-5-carboxylic acid ethyl ester:

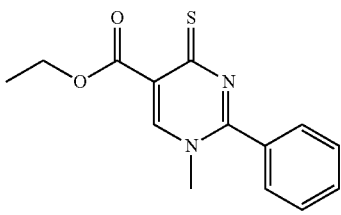 [SMILES: CCOC(=O)c1cn(C)c(-c2ccccc2)nc1=S]

5-methyloxazolidine-2-thione:

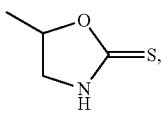

or 1-(3,5-dicarboxyphenyl)-5-mercaptotetrazole

A stable source of metal for antimicrobial devices which is a stable-metal-organic complex of metal suitable for antimicrobial devices with a thiazoline-thione or thiazolidine thione is represented by the structure:

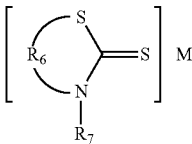

(V)

wherein $R_6$ represents atoms completing a heterocyclic ring, such as

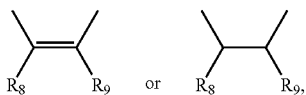

wherein $R_8$ and $R_9$ are the same or different, and each is hydrogen, alkyl; especially alkyl containing one to five carbon atoms, such as methyl, ethyl, propyl, butyl and pentyl; aryl, as described; carboxyl; hydroxyl; sulfonic acid; and mercapto; $R_7$ is hydrogen, alkyl, as described, typically alkyl containing one to five carbon atoms, aryl, especially containing six to 20 carbon atoms, carboxyl or sulfonic acid, as described.

Examples of suitable metal thiazoline thione complexes which are stable sources of silver, copper, or zinc for antimicrobial devices are stable silver, copper or zinc complexes of the following compounds: 3-carboxymethyl-4-methyl-thiazoline-2-thione, 3-(2-carboxyethyl)-4-methyl-thiazoline-2-thione, 3-(3-carboxypropyl)-4-methyl-thiazoline-2-thione, 3-(4-carboxybutyl)-4-methyl-thiazoline-2-thione, 3-(5-carboxypentyl)-4-methyl-thiazoline-2-thione, 3-carboxymethyl-4-methyl-5-carboxy-thiazoline-2-thione, 3-(2-carboxyethyl)-4-methyl-5-carboxy-thiazoline-2-thione, 3-(3-carboxypropyl)-4-methyl-5-carboxy-thiazoline-2-thione, 3-carboxymethyl-4-methyl-5-carbethoxy-thiazoline-2-thione, 3-(2-carboxyethyl)-4-methyl-5-carbethoxy-thiazoline-2-thione, 3-(3-carboxypropyl)-4-methyl-5-carbethoxy-thiazoline-2-thione, 3-carboxymethyl-4-carboxymethyl-thiazoline-2-thione, 3-(3-carboxypropyl)-4-carboxymethyl-thiazoline-2-thione, 3-carboxymethyl-4-methyl-5-acetyl-thiazoline-2-thione, 3-(2-carboxyethyl)-4-methyl-5-acetyl-thiazoline-2-thione, 3-sulfoethyl-4-methyl-thiazoline-2-thione, 3-(m-carboxyphenyl)-4-methyl-thiazoline-2-thione, 3-(1-carboxyethyl)-4-carboxy-thiazoline-2-thione, 3-(1-carboxyethyl)-4-carbethoxy-thiazoline-2-thione, 3-(1-carboxyethyl)-4-(carbethoxymethyl)-thiazoline-2-thione, 3-(2-carboxyethyl)-4-(carbethoxymethyl)-thiazoline-2-thione, 3-(2-carboxyethyl)-4-(n-butylsulfonymethyl)-thiazoline-2-thione, 3-(1,2-dicarboxyethyl)-4-methyl-thiazoline-2-thione, or 4-carboxy-thiazoline-2-thione.

Examples of suitable metal thiazolidine thione complexes which are stable sources of silver, copper, or zinc for antimicrobial devices according to the present invention are metal complexes of thiazolidine thione compounds corresponding to the described thiazoline thione compounds. For instance, suitable metal thiazolidine thione complexes include stable silver, copper or zinc complexes of the following compounds: 3-carboxymethyl-thiazolidine-2-thione, or 3-carboxyethyl-thiazolidine-2-thione.

A stable source of metal for antimicrobial devices which is a stable metal-organic complex of a metal suitable for antimicrobial devices with a thiopyrimidine is represented by the formula:

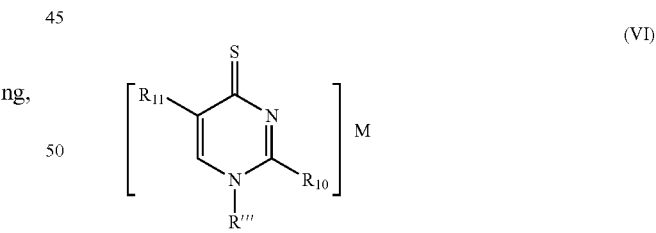

(VI)

wherein M is as described; $R_{10}$ and R'" are individually hydrogen, alkyl or aryl as described, especially phenyl; $R_{11}$ is hydrogen, carboxy, alkyl or aryl, as described.

Examples of suitable silver-thiopyrimidine complexes which are stable sources of silver for antimicrobial devices are stable silver complexes of 5-carboxy-2-phenyl-4-thiopyrimidine, or 5-carbethoxy-1-methyl-2-phenyl-thiopyrimidine.

A stable source of metal for antimicrobial devices which is a stable metal-organic complex of a metal suitable for antimicrobial devices with an oxazolidine-2-thione is represented by the formula:

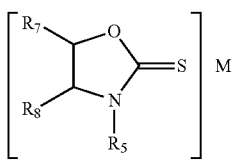

wherein M, $R_5$, $R_6$ and $R_7$ are as described.

Examples of suitable silver-oxazolidine-2-thione complexes which are stable sources of silver for antimicrobial devices are 5-methyloxazolidine-2-thione, or 5-carbethoxyoxazolidine-2-thione.

A stable source of metal for antimicrobial devices which is a stable metal-organic complex of a metal suitable for antimicrobial devices with a dithiocarbamate is represented by the formula:

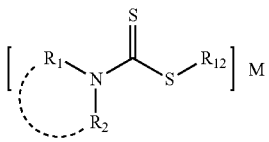

wherein M, $R_1$ and $R_2$ are as described; and $R_{12}$ is alkyl, aryl, as described, or carboxyaryl, or carboxyalkyl, e.g., containing six to 20 carbon atoms, such as carboxybenzyl, carboxyxylyl or carboxyphenyl.

Examples of suitable silver-dithiocarbamate complexes which are stable sources of silver for antimicrobial devices are stable silver complexes of 4-carboxybenzyl-dimethyl dithiocarbamate, or 4-carboxyphenyl-dimethyldithiocarbamate.

A further stable source of metal for antimicrobial devices is a stable metal-organic complex of a metal suitable for antimicrobial devices with a thiourea derivative represented by the formula:

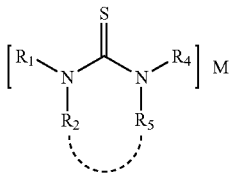

wherein M, $R_1$, $R_2$, $R_4$ and $R_5$ are as described; and $R_2$ and $R_5$ can, but need not, be joined to form a heterocyclic ring, represented by the broken line in Structure VI. $R_2$ and $R_5$ when joined to form a heterocyclic ring can be, for example,

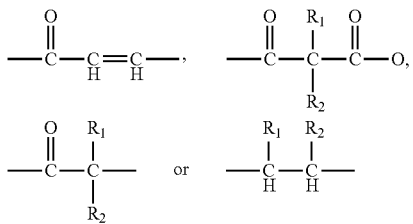

wherein $R_1$ and $R_2$ are as described.

Examples of suitable stable sources of silver for antimicrobial devices are complexes of silver with 2-thiouracil, thiobarbituric acid, imidazolidine-2-thione, 1,3-diethyl-2-thiobarbituric acid, or 1,3-bis(2-carboxyphenyl)-1,3-dimethylthiourea.

A stable source of metal for antimicrobial devices which is a stable metal-organic complex of a metal suitable for antimicrobial devices with a guanyl-containing compound is represented by the formula:

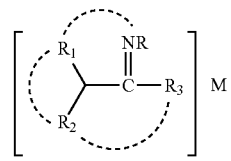

wherein M, $R_1$, $R_2$ and $R_3$ are as described; R is hydrogen, alkyl or alkylene as described; and any two of the described R groups can be, but need not be, joined to form a heterocyclic ring.

An example of a stable metal-organic complex of a metal suitable for antimicrobial devices within structure VII is a stable metal-organic complex of a metal suitable for antimicrobial devices with a pseudothiohydantoin represented by the formula:

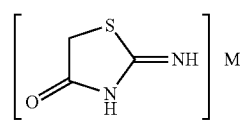

wherein M is as described, especially silver.

A further source of metal for antimicrobial devices is a stable metal-organic complex of a metal suitable for antimicrobial devices with an imidazolidine, especially a 2-thioimidazolidine represented by the formula:

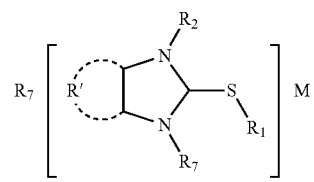

wherein M, $R_1$, $R_2$ and $R_7$ are as described; R' is hydrogen or atoms completing a hydrocarbon ring, e.g., alkylene containing four to eight carbon atoms completing a benzene or naphthylene ring, and their corresponding tautomers.

Examples of suitable stable silver-imidazolidine complexes as stable sources of silver for antimicrobial devices are complexes of silver with imidazolidine-2-thione or 1,3-bis(2-carboxyethyl)-benzimidazole-2-thione.

A source of metal for antimicrobial devices is a stable metal-organic complex of a metal suitable for antimicrobial devices with an imidazoline, especially a 2-thioimidazoline represented by the formula:

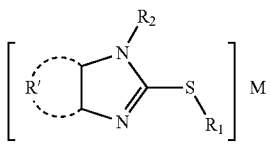
(XIII)

wherein M, $R_1$, $R_2$ and R' are as described, and their corresponding tautomers.

Examples of suitable stable silver-imidazoline complexes as stable sources of silver for antimicrobial devices are complexes of silver with 2(2-carboxyethylthio)-[Dgr].sup.2-imidazoline, or 2(2-carboxypropylthio)-[Dgr].sup.2-imidazoline.

A further source of metal for antimicrobial devices is a stable metal-organic complex of a metal suitable for antimicrobial devices with an isothiourea derivative represented by the formula:

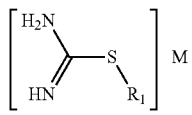
(XIV)

wherein $R_1$ and M are as described, with the exception that $R_1$ is not hydrogen, $R_1$ typically being carboxyalkyl or sulfoalkyl. This formula does not include thiourea.

Examples of suitable stable silver-isothiourea derivative complexes as stable sources of silver for antimicrobial devices are complexes of silver with S-(carboxymethyl)isothiourea, S-(2-carboxyethyl)isothiourea, S-(3-carboxypropyl)isothiourea, S-(2-carboxylsopropyl)isothiourea, or S-(3-sulfopropyl)isothiourea.

A stable source of metal for antimicrobial devices is a stable metal-organic complex of a metal suitable for antimicrobial devices with a mercapto acid, especially a mercapto carboxylic acid represented by the formula:

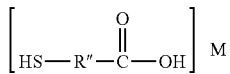
(XV)

wherein M is as described and R" is alkylene, such as alkylene containing one to 20 carbon atoms, typically alkylene containing one to five carbon atoms, such as methylene, ethylene, propylene, butylene, pentylene, decylene and eicosylene. R" can contain substituent groups which do not adversely affect developing action of the described compounds such as alkyl, e.g., alkyl containing one to 20 carbon atoms, typically alkyl containing one to five carbon atoms as described, carboxy, sulfonic acid, mercapto and amino.

Examples of stable silver mercapto acid complexes which are stable sources of silver for antimicrobial devices according to the invention are silver complexes of mercaptoacetic acid, mercaptopropionic acid, mercaptoisobutyric acid, mercaptosuccinic acid, alpha-mercaptoadipic acid, or L-cysteine.

A stable source of metal for antimicrobial devices is a stable metal-organic complex of a metal suitable for antimicrobial devices with a mercaptoacetyl amide represented by the formula:

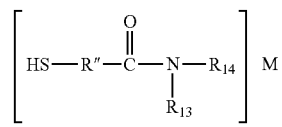
(XVI)

wherein M and R" are as described; $R_{13}$ and $R_{14}$ are the same or different and each selected from hydrogen; lower alkyl, as described; mercapto; carboxyl; sulfonic acid; hydroxyl and phenyl; at least one of $R_{13}$ and $R_{14}$ being phenyl. The phenyl group can contain various substituent groups which do not adversely affect the stability and availability of metal for antimicrobial devices, such as carboxyl, hydroxyl, sulfonic acid, and the like.

Examples of silver-mercaptoacetanilide complexes which are stable sources of silver for antimicrobial devices include silver complexes of mercaptoacetanilide, mercaptomethylacetanilide, or mercapto aceto-p-toluidide.

A metal-alkyne complex which is a stable source of metal for antimicrobial devices according to the invention is represented by the formula:

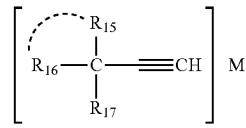
(XVII)

wherein M is a metal suitable for antimicrobial devices, as described; $R_{15}$ is hydrogen, aryl, as described, alkyl, as described, or alkylene, also as described, forming a ring with $R_{16}$, as represented by the broken lines in Structure XIV; $R_{16}$ is hydrogen, aryl, alkyl, as described, or alkylene, also as described, forming a ring with $R_{15}$; $R_{15}$ and $R_{16}$ together may represent a keto oxygen; $R_{17}$ is —O—$R_{18}$, —S—$R_{19}$,

or an alkylene oxide polymer adduct represented by the formula:

—O(CH$_2$CH$_2$O)$_n$H wherein n is an integer, such as an integer from 1 to about 100 or more; $R_{18}$, $R_{19}$, $R_{20}$ and $R_{21}$ are the same or different and each selected from hydrogen, acyl or alkyl, as described, typically alkyl containing one to five carbon atoms.

Examples of silver-alkyne complexes suitable according to the invention are silver complexes of 3-methyl-1-butyn-3-ol, 3-methyl-1-pentyn-3-ol, 1-hexyn-3-ol, 4-t-butyl-1-ethynylcyclohexanol, 3,5-dimethyl-1-hexyn-3-ol, 3-(p-chlorophenyl)-1-butyn-3-ol, ethylene oxide adduct of 3-methyl-1-butyn-3-ol:

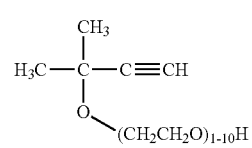

ethylene oxide adduct of 3-methyl-1-pentyn-3-ol:

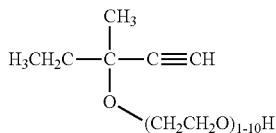

1-ethynylcyclopentanol:

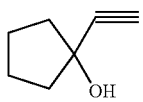

1-ethynylcyclohexanol:

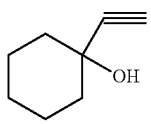

ethylene oxide adduct of 1-ethynyl-cyclohexanol:

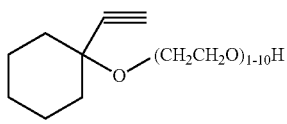

2-propynyl cyclohexylcarboxylate:

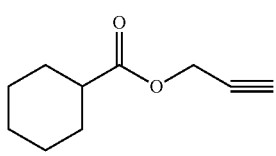

3-(diethylamino)-1-butyne:

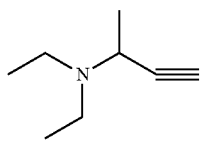

methyl propiolate:

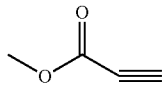

4-(1-hydroxy-2-propynyl)cyclohexene:

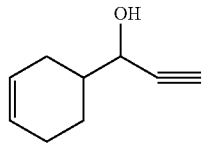

3-cyclopropyl-1-butyne-3-ol:

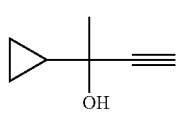

3-phenyl-1-propyn-3-ol:

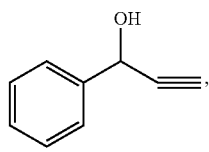

and ethylene oxide adduct of 3-methyl-1-nonyn-3-ol:

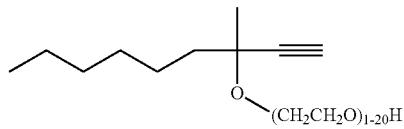

A metal-hydroxyalkyl carboxylic acid complex or metal-hydroxy heterocyclic carboxylic acid complex which is a stable source of metal for antimicrobial devices according to the invention is represented by the formula:

[HO—W—COOH]M (XVIII)

wherein M is as described and W is alkylene, as described, or a heterocyclic group, typically a five- or six-membered heterocyclic ring, e.g., a triazaindene or a tetraazaindene ring system. The described alkylene and heterocyclic groups can contain various substituent groups, such as alkyl or aryl as described, carboxyl, hydroxyl, sulfonic acid, and the like.

Examples of suitable silver-hydroxy alkyl carboxylic acid complexes according to the invention are silver complexes of glycolic acid, lactic acid, methyl lactic acid, malic acid, tartaric acid, citric acid, 3,5-dihydroxybenzoic acid, benzilic acid:

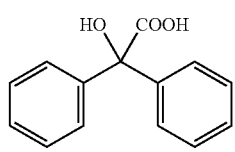 [SMILES: O=C(O)C(O)(c1ccccc1)c1ccccc1]

tetrahydroxysuccinic acid

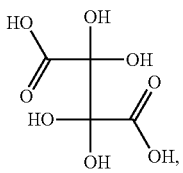

and 12-hydroxystearic acid

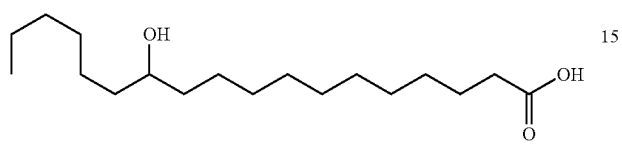

An example of suitable silver hydroxy heterocyclic carboxylic acid complexes according to the invention is a silver complex with 6-carboxy-7-hydroxy-1,3a,4-triazaindene:

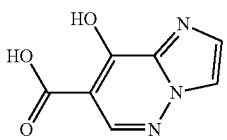

A stable source of metal for antimicrobial devices is a stable metal-organic complex of a metal suitable for antimicrobial devices with a thiaalkyl compound of the formula:

[X—S—Z]M     (XIX)

including a dithiaalkyl compound of the formula:

[X—S—S—Z]M     (XX)

and/or an oligothiaalkyl compound of the formula:

[X—S—(Y—S)$_n$—Z'] M     (XXI)

wherein X and Z are the same or different and each is heterocyclic, aryl, alkyl or acyl, as described; Z' is Z or hydrogen; n is a number, e.g., 1 to 10 inclusive typically 1 to 5; Y is alkylene, as described; and M is a metal suitable for antimicrobial devices, as described, especially silver.

Heterocyclic, as described herein, includes any heterocyclic group which does not cause undesirable fog or stain and does not adversely affect desired antimicrobial devices, for example, heterocyclic groups represented by the formulas:

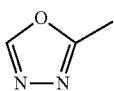 (1)

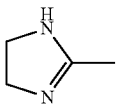 (2)

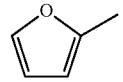 (3)

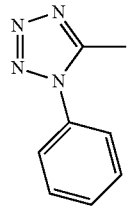 (4)

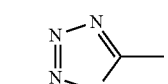 (5)

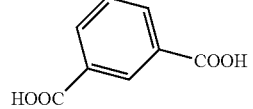

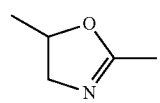 (6)

Examples of other suitable silver-organic complexes which are stable sources of silver for antimicrobial devices within the described formulas are silver complexes with the following compounds. Some of these can be classified in one or more of the described formulas.

1-(3,5-dicarboxyphenyl)-5mercaptotetrazole

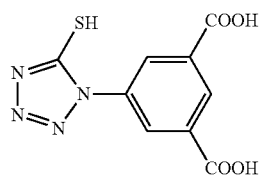 [SMILES: O=C(O)c1cc(C(=O)O)cc(-n2nnnc2S)c1]

D-xylose diethyl mercaptal:

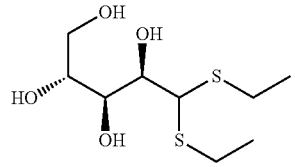

5,5'-dithiobis(1-phenyltetrazole):

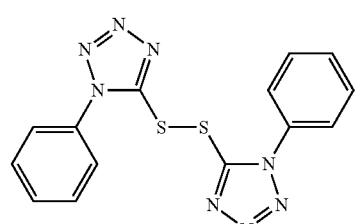

11,14,17,20-tetrakis(hydroxymethyl)-13,16,19-trioxa-4,7,10-trithia-1,2,22-docosanetriol:

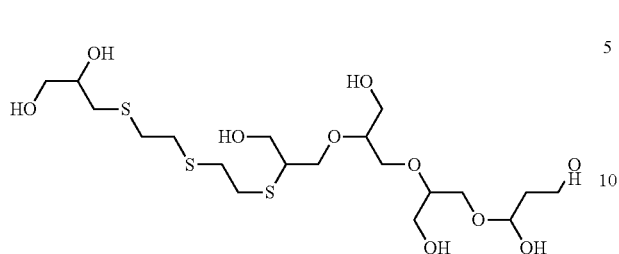

2-hydroxyethylamino oligoethylene sulfide:

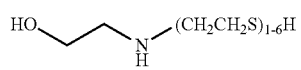

4-(hydroxymethyl)cyclohexylmethyl-amino oligoethylene-sulfide:

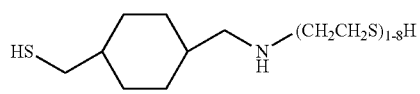

2-(carboxymethylthio)-5-phenyl-1,3,4-oxadiazole:

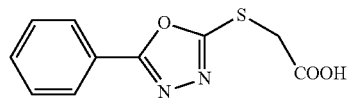

5,5'-thiodisalicylic acid:

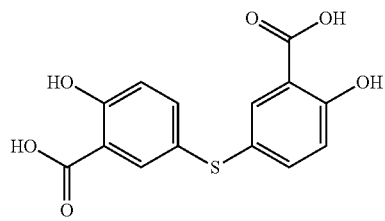 [SMILES: O=C(O)c1cc(Sc2ccc(O)c(C(=O)O)c2)ccc1O]

4-(1,2-dicarboxyethylthio)-5-phenylcatechol:

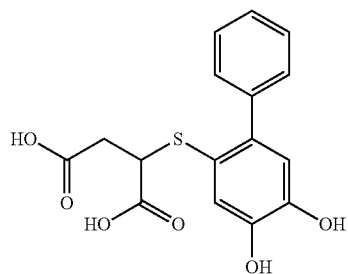 [SMILES: O=C(O)CC(Sc1cc(O)c(O)cc1-c1ccccc1)C(=O)O]

S-(o-carboxyphenyl)thioglycolic acid:

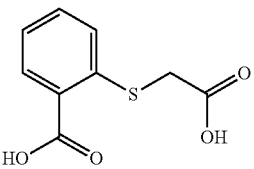

4-(methylthio)phenol:

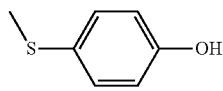

phenylthioacetic acid:

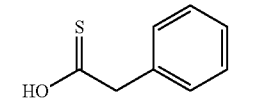

4-(carboxymethylthio)aniline:

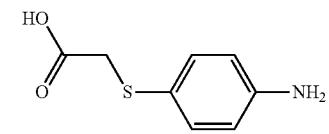 [SMILES: Nc1ccc(SCC(=O)O)cc1]

3-thiavaleric acid

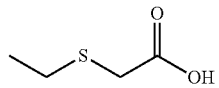

2-(2-furylthio)benzoic acid

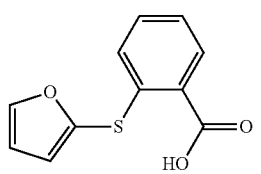 [SMILES: O=C(O)c1ccccc1Sc1ccco1]

(2-furylthio)acetic acid

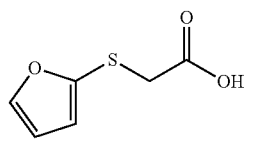

2(2-furylthio)propionic acid
3-(2-furylthio)propionic acid
(2-furylthio)succinic acid An especially useful stable source of metal for antimicrobial devices is a stable metal-organic complex of a metal suitable for antimicrobial devices with a polymer containing a ligand atom having the property of forming a complex with the described metal. The described polymer includes any polymer which provides the desired complex, does not cause undesired fog or stain and releases the described metal for antimicrobial devices. These include homopolymers and copolymers, which include interpolymers of various monomeric and polymeric units. These can contain one or more of the same ligand atom or different ligand atoms. The metal released may be the metallic or the ionic form.

Any ligand atom is suitable which provides the desired complex. Ligand atoms are described in the book, "Organic Complexing Reagents" by D. D. Perrin, Interscience Publishers, Division of Wiley and Co., 1964, especially the first three chapters. Suitable polymers containing ligand atoms are described, for example, in the book "Vinyl and Related Polymers" by C. D. Shildknecht, John Wiley and Sons, 1952. Especially suitable polymers are those which provide the advantage of serving as a stable source of silver, copper or zinc for antimicrobial devices.

A suitable stable metal-organic complex of a metal suitable for antimicrobial devices with a polymer containing a ligand atom is a metal-organic complex of a metal suitable for antimicrobial devices, especially silver, copper or zinc, with a polymer containing thiaalkylacrylamide units and/or thiaalkylmethacrylamide units, such as represented by the formula:

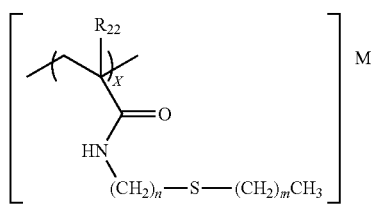

wherein M is as described; $R_{22}$ is methyl or hydrogen; n is a number especially 1 to about 10; m is 0 to about 10; and x is a number of 2 or more, e.g., usually sufficiently high to provide an average molecular weight of about 1,000 to about 1,000,000.

Another suitable stable metal-organic complex of a metal suitable for antimicrobial devices with a polymer containing a ligand atom is a metal-organic complex of a metal suitable for antimicrobial devices, especially silver, copper or zinc with a polymer containing thiaalkylacrylate units and/or thiaalkylmethacrylate units such as represented by the formula:

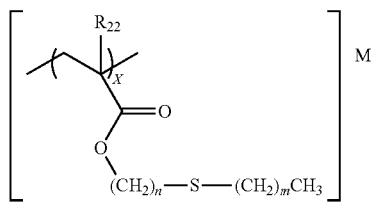

wherein M, $R_{22}$, n, m and x are as described.

Examples of suitable metal-organic complexes according to the invention wherein the organic moiety is a described polymer include silver complexes with:

a terpolymer of (a) 3-thiapentylacrylate, (b) acrylic acid, and (c) 3-acryloxypropane-1-sulfonic acid sodium salt;

a copolymer of (a) 3-thiapentylmethacrylate and (b) 3-acryloxy-propane-1-sulfonic acid sodium salt;

a terpolymer of (a) N-3-thiabutylacrylamide, (b) acrylamide, and (c) 2-methacryloxyethyl acetoacetate; and/or a copolymer of (a) S-2-methacryloxyethylisothiuronium methane-sulfonate and (b) 3-acryloxypropane-1-sulfonic acid sodium salt.

These polymers have a wide range of average molecular weight, but usually have an average molecular weight of about 100,000 or more.

The described polymers can be prepared employing methods of polymerization known in the art, e.g., such as methods set out in the described Schildknecht reference.

The invention includes other equivalent suitable sources of silver for antimicrobial devices such as stable silver-organic complexes which are complexes of silver with the following compounds:

1,10-phenanthroline:

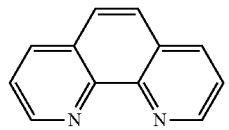 [SMILES: c1cnc2c(c1)ccc1cccnc12]

1(4-carboxyphenyl)-3,5-dimethyl-4-phenylpyrazole:

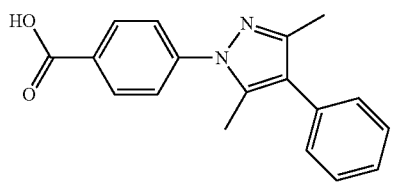 [SMILES: Cc1nn(-c2ccc(C(=O)O)cc2)c(C)c1-c1ccccc1]

Sodium dicyanamide:

8-hydroxyquinoline:

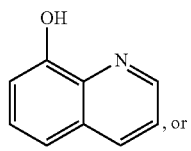 [SMILES: Oc1cccc2cccnc12 ; ", or"]

, or 8-hydroxyquinoline sulfate:

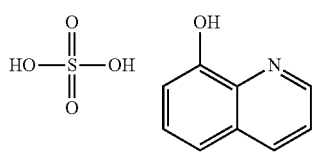

Combinations of metal complexes can be employed according to the invention, such as combinations of silver complexes with gold, platinum or palladium complexes, or combinations of different organic complexing moieties, such as combinations of thiazoline thiones with alkynols or different thiazoline thiones with each other.

Preparation of Silver Compounds

The present invention comprises methods of preparation of antimicrobial silver compounds. In one embodiment, silver compounds are identified as ionic salts. Silver compounds M+X− under group A can be prepared in relatively straightforward manner. Compounds with imides having an increased acidic proton or decreased solubility in water are useful. To illustrate one method, the preparation of silver saccharinate from sodium saccharinate is provided. The following chemical reaction takes place.

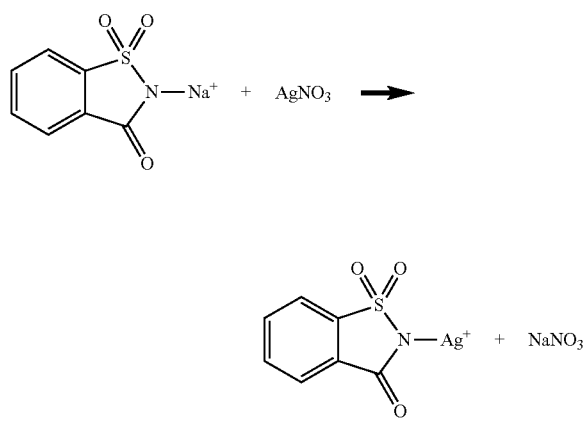

To a solution of sodium saccharinate of appropriate molarity (0.125 or more), a solution of soluble silver nitrate of the same or slightly lower molarity (5 to 10% lower molarity) was added to precipitate weakly soluble silver saccharinate that was recovered by washing with deionized water which dried to a white powder in good yields (>80%). An advantage of working with silver saccharinate is the preparation steps can be carried out in ambient light. No protection against light is needed as silver saccharinate powder is not very light sensitive.

Silver saccharinate can be also prepared directly from saccharin. This method is described in U.S. Pat. No. 3,152,904 where silver saccharin was formed by treating a solution of saccharin in hot xylene with aqueous silver nitrate in a two-phase reaction system. Other aprotic solvents such as THF can also be used in place of xylene. In general, in the preparation of silver compounds MX of group A type, silver from soluble salt is exchanged with alkali or alkaline earth cation or hydrogen to yield insoluble silver salt of the imide. Neat solvents or the mixtures of water, lower alkyl alcohols, lower branched alcohols, THF, acetone and other suitable solvents may be used in the preparation. Generally the preparation is carried out at ambient temperature but different temperatures may also be employed.

The preparation of silver compounds MX of groups B and C are quite similar to those of group A. For example, thiobarbitutric acid (group B) is first converted to its alkali metal salt and mixed with solution of silver nitrate to precipitate insoluble silver thiobarbiturate (see chemical reactions below) that is recovered after filtration and drying. Likewise, silver behenate (Group C) can be readily formed by mixing sodium behenate and silver nitrate solutions according to a method described in example 5 in U.S. Pat. No. 3,152,904 which is fully incorporated herein by reference.

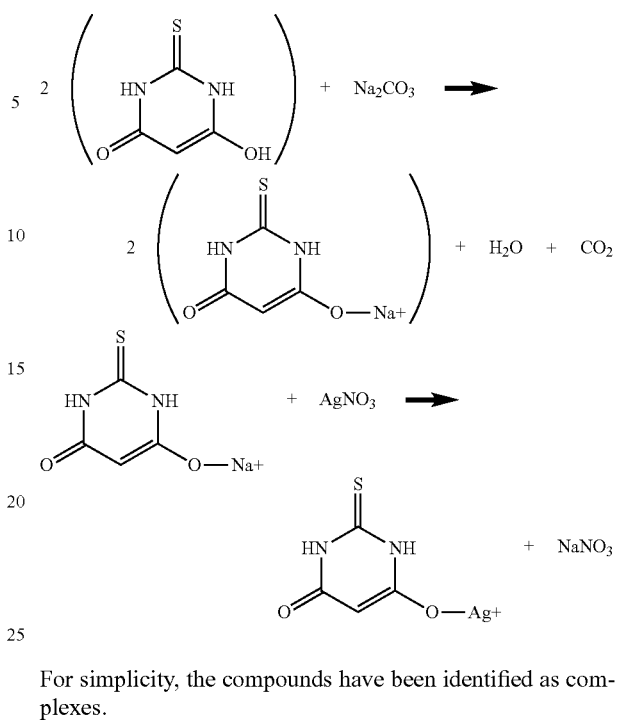

For simplicity, the compounds have been identified as complexes.

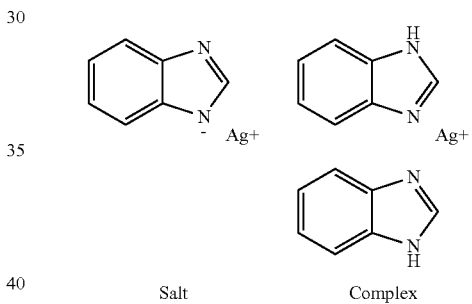

Salt   Complex

The silver complexes M[Y] are readily prepared by known precipitation methods. For instance, silver benzimidazole complex was prepared by mixing an alcoholic solution of benzimidazole and an aqueous solution of silver nitrate in stoichiometric proportion. Upon mixing a white precipitate was formed that is recovered after filtration and drying. The white powder remained unchanged even after prolonged exposure to room light. Solvents suitable for use in the preparation of silver complexes include but are not limited to water, lower alkyl alcohols, lower alkyl branched alcohols, THF, acetone, toluene, xylene or their mixtures in desired proportions.

Generally in any of the above preparations, ambient temperatures 25° C. to 35° C. are preferred but higher temperatures may also be employed without departing from the scope of the invention. To compensate for any exothermic reaction, preparation may also be carried out below room temperature.

The mixing of the organic compound or its salt and silver nitrate can be carried out in any order. Though, the addition of silver salt solution to the organic compound or its salt is preferred. Stirring may be used. Stoichiometric proportions of the reagents may be generally employed but slight excess in favor of the anion providing the compound or the complexing compound is favored for more complete conversion of silver cations to weakly soluble form.

From reaction mixtures, the silver compounds may be recovered in solid form or may be used as suspension in subsequent steps. In solid form, it is not important for the practice of the invention that the compounds be recovered as crystals or as amorphous powder. However, it is useful that in solid form the silver compounds be present as finely dispersed particles.

The silver compounds taught herein may be used individually or in combination with other compounds taught herein, and with other active agents. Such compounds, alone or in combination with active agents, may be admixed with compositions and such compositions may be used as treatment devices, or may be added to medical devices. The compounds taught herein, singly or in combination with active agents, alone or in compositions, may be added to fibers, substrates or other surfaces to render such surfaces antimicrobial. Such antimicrobial surfaces may be wound care devices, medical devices, patient care devices or other devices or surfaces where microbial growth is not desired.

Examples of active agents providing antimicrobial action include but are not limited to isoniazid, ethambutol, pyrazinamide, streptomycin, clofazimine, rifabutin, fluoroquinolones, ofloxacin, sparfloxacin, rifamin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclarazil, acyclovir, trifluorouridine, foscarnet, penicillin, gentamicin, ganciclovir, iatroconazole, miconazole, zinc-pyrithione, heavy metals including but not limited to platinum or gold, and their combined forms including salts such as halides, saccharinates and complexes with carriers and other forms, or nanoparticles of silver, zinc and copper.

Silver polymer compounds may be prepared from many known methods. Polymers having saccharin, benzimidazole and imidazole moieties are useful for making silver compounds of the present invention. For example, the silver polymeric compounds can be prepared from any end group terminated polymer capable of coupling with amine group and a saccharin sodium salt derivative having an amine group on the aromatic ring. Pre-polymers capable of further reactions are available commercially. Suitable groups reactive to amines are isocyanate, isothiocyanate, carboxylic acid, halocarbonyl and others. Pre-polymers can be polyurethanes, polyethers, polyacrylates, polysiloxanes or others. Amino saccharin can be prepared following the procedure described by Rose & Sanford (J. Chemical. Edu., Volume 47 (no. 9), p 649-50 (1970) and fully incorporated herein by reference. The resulting polymer with saccharin moiety can be then converted to silver containing polymer by treatment with a silver salt solution (e.g. silver nitrate or perchlorate).

Alternatively, amino saccharin can be treated with a polymer having an acid chloride group containing a polymer to link the saccharin moiety to the polymer via amide link. By treating with a soluble silver salt solution, the resulting polymer can be converted to incorporate bound silver. By treating chloromethyl groups containing polymer with benzimidazole or imidazole attaches the heterocyclic moieties to the polymer. Subsequent treatment with silver salt solution adds silver to the polymer.

Maleic anhydride homopolymers or copolymers can be converted to corresponding maleimide polymers that then can be incorporated with silver by treating them with silver salt solution. It is to be understood that, none of above examples are to be taken as limiting the scope of the invention. To the contrary, the selection of a given prep-polymer or given coupling chemistry is merely to illustrate one element of an embodiment of the invention. For preparation of other compounds see U.S. Pat. Nos. 3,689,486; 3,142,904; 3,933,507; 4,260,677; 5,863,864, all of which are herein incorporated in their entirities.

Antimicrobial Wound Care Devices

Generally stated, any wound care device can be rendered antimicrobial using the silver compounds of the present invention. Devices may be dry, as in not containing moisture, or may contain moisture. In use, the devices may be placed in a moisture rich environment or in environments where some moisture may be available, which allows for the release of antimicrobial silver. Such devices may comprise hydrophilic matrices comprising, for example, cellulose ether derivatives, hydroxyl alkyl cellulose ether derivatives, hydroxyl alkyl cellulose derivatives or mixtures thereof, cotton, rayon, acrylics, acetate fibers, alginates and other synthetic and natural polymers and their blends, moisture containing wound dressings, skin contact devices such as monitor leads, wound dressings, hydrated plastic implants, hydrocolloid dressings, dressings used in wet therapy, super-absorbent foams, hydrophilic polyurethane foams, activated charcoal dressings, compresses, xeroform petrolatum dressings, venous, urinary and pain management system catheters, stents, guidewires, shunts, cannulae, catheter adapters and other solid and hollow tubular devices, molded articles such as tracheal tubes, contact lens cases, nebulizers, sutures, incontinence products and feminine hygiene products, ostomy pouches and plugs, respiratory and feeding appliances, contact lenses, hearing aids, haemostats, and urine collection bags as examples.

An aspect of the present invention comprises antimicrobial traditional woven cotton gauzes, and other suitable woven materials like polyesters, rayon, acetate, nylon and nylon blends with cotton can also be used. Gauzes are used in wound management for example to wrap the bandages that cover the wound or clean and prepare a wound for routine cleaning and washing treatment. Gauzes help keep the bandages in place and absorb any excess wound exudate that may leak from wounds. Gauzes may be single ply or multi-ply. The numbers of ply are not limiting in the practice of the present invention, and any woven or nonwoven material, used in this fashion, that can be rendered antimicrobial using the methods of the present invention, are contemplated herein. Gauze material may be dyed with color or bleached plain white. Those skilled in the art will recognize that the ply number of cotton gauze material is immaterial to the practice of the invention. Though the preferred gauze material has ply number between 1 and 6 (both inclusive). However this range of gauze ply number should not be construed as limiting. Silver treated gauze materials with higher ply numbers are also within the scope of the present invention.

Antimicrobial treatment of the gauze materials such as woven or non-woven can be carried out by different methods. One illustrative method used is as follows. Dry cotton gauze material was soaked in the aqueous solution of silver nitrate, blotted to remove excess liquid then soaked in the second solution of sodium saccharinate, re-blotted to remove excess liquid and dried. Dipping in the second solution precipitated fine silver saccharinate particles onto the gauze fibers. The method can be applied to treat woven or non-woven materials made from rayon, acrylics, polyester and their blends with cotton. In the alternative, for instance, the gauze material can be treated first with sodium saccharinate and then treated with silver nitrate solution with the blotting steps remaining unchanged. In another method of preparing antimicrobial gauze material, a suspension of silver saccharinate was pre-made by mixing solutions of silver nitrate and sodium saccharinate in the presence of surfactants such as polysorbates. Dry gauze material was then dipped in the silver suspension, blotted and dried in the oven.

In these methods, silver nitrate solution concentrations may range from about 0.001 M to about 2.0 M, from about 0.01 M to about 0.5 M, from about 0.05 M to about 1.5 M, from about 0.01 to about 1.0 M, from about 0.001 to about 1.0 M, and from about 1.0 M to about 2.0 M, and from 0.001 to about 0.5 M. Sodium saccharinate concentration scan range from about 0.0008 M to about 3.0 M, from about 0.01 M to about 0.75 M, from about 0.001 to about 2 M, from about 0.01 to about 1 M, from about 0.0001 to about 0.01 M, and from about 2 M to about 3 M.

Surfactants play a useful role in the preparation of the suspension as the surfactants help keep the particles of silver saccharinate below certain size and also prevent or retard their agglomeration. Surfactants can come from classes other than polysorbates but are surfactants that are generally soluble in water or in water-organic solvent mixtures are useful. Surfactants include polysorbates such as Tween 20. Surfactant concentration in silver saccharinate suspension can vary between 0.5 gm/liter and 100 gm/liter and is preferably between 2 gm/liter and 8 gm/liter with a range of 4 to 6 gm/liter being most suitable. The mode of contact of gauze material with the silver salt solution and sodium saccharinate solution is not limited to soaking. The contact can be made in various ways that are known to those ordinarily skilled in the art. For example, solutions can be sprayed or dripped onto the gauze. Further, the blotting step described here to remove excess liquid from gauze is also not limiting. Liquid removal can be carried out by squeezing the gauze between pair of rollers or by centrifuge operation and other processes used in the textile industry. Besides sodium, other saccharinates of potassium, calcium, lithium can be used. As a source of silver ions, many soluble silver salts including but not confined to those of nitrate, acetate, lactate, citrate, and perchlorate can be used. Generally, a molar excess of saccharinate over silver is used to ensure complete conversion of silver to the silver saccharinate complex, though less than or equal to a stoichiometric amount can also be used. If a very low mole ratio of sodium saccharinate to silver salt is used, the treated device may show some discoloration upon light exposure from residual silver nitrate. Therefore, mole ratios of saccharinate to silver less than 0.8 may not be suitable for some treatments of gauze materials. Typically the present invention contemplates a molar excess ratio between 0.8 and 2.0 though ratios higher than 2.0 are not outside the scope of the invention. A useful mole ratio is between 1 and 1.5. The use of water as a solvent in the preparation of salt solutions is also not restrictive, and any solvent that adequately dissolves the compounds is contemplated by the invention.

Many materials used for medical and wound care products are intended to gel in the presence of water. This property interferes with methods of making the material antimicrobial using water-containing solutions, and can be overcome by using a non-aqueous vehicle during the treatment of the materials with silver compounds. Solvents that can be used in mixtures with water in the practice of the invention are lower alkyl straight chain and branched alcohols (C1 to C5), acetone, methyl ethyl ketone, diacetone alcohol, ethyl acetate and tetrahydrofuran. Other solvents that are generally miscible with water can be also employed. Organic solvents alone (without water) can also be used in the present invention. Useful solvents are water, ethanol, isopropanol and acetone. The composition of water and organic solvents mixture, such as water and ethanol, water and isopropanol, or water and acetone, can vary from 0% water to 100% water with water between 0% and 50% useful.

The silver loading, or the amount of silver in a finished product, whether it is a device or composition, of a given antimicrobial device is generally determined by how the amount of time the device will be in use. Thus it is desirable to control the duration over which the sustained release of antimicrobial silver is effective. The need for activity over 5 days of use requires higher amounts of total silver than a device used for a shorter amount of time. In an antimicrobial medical device of the present invention, silver content can vary between 50 ppm to 50,000 ppm (ppm as measured based on the weight of the device), though even higher amounts can be considered within the scope of the invention. Silver content for cotton gauze materials for sustained release activity for 5 to 7 days may be between 2000 and 10,000 ppm. The ply number of cotton gauze material is immaterial to the practice of the invention.

Methods of drying gauze materials by exposure to high temperature environments are also not limiting. Other types of drying processes such as infrared, contact drying, steam drying, and freeze drying can be employed in the practice of the invention. The drying temperature is determined by the reasonable duration available for drying and the sensitivity of the silver compound impregnating the gauze material to heat. The drying temperature for silver containing gauze material is between 25° C. and 135° C. In the case of silver saccharinate containing gauze materials, brief exposure to higher temperatures up to 150° C. can be tolerated.

Examples of successful silver treatment of fabric materials rendered antimicrobial used the commercially available products Bulkee II®, Avant® cotton/rayon drain sponges, Sofform® polyester bandages, Ready Bath® body wipe cloth from Medline Industries, Mundelein Ill. and Curity® gauze from Tyco Healthcare Company, Mansfield, Mass. as the stock matrix.

The antimicrobial activity can be imparted to a variety of wound care devices having different end uses. One can treat collagen based matrix, superabsorbent dressing materials such as carboxy methyl cellulose/alginate fiber sheets, acrylate-based super absorbents used in diapers and other incontinence devices, alginate fibers sheets and tows, modified cellulose fiber materials, bamboo fiber materials, alginate foam sheets, hydrophilic polyurethane foams, alginate powder and chitosan powder. Select examples that are commercially available include Maxorb® carboxy methyl cellulose/alginate fiber sheets from Medline Industries, alginate fiber sheets from AMS of UK and DeRoyal Inc of Tennessee, alginate fiber tow from MedTrade Ltd of UK, DeRoyal Inc. of Tennessee, Tegagen® from 3M of Minnesota, alginate foam sheets from Kuraray Industries of Japan, alginate powder from Sigma-Aldrich Co. and hydrophilic foam materials Rynel 562 from Rynel Corporation, Maine and Prepol® based foams from Lendell Manufacturing Inc. of Michigan. Example of collagen based matrix amenable to silver treatment by the present invention is Integra® bilayer matrix wound dressing from Integra Lifesciences New Jersey.

In the treatment of the aforementioned matrices with the exception of collagen and polyurethane foams matrices, the salt solutions are preferably made in non-aqueous solvents or predominantly non-aqueous solvents because of the tendency of these matrices to absorb water. Those familiar with these matrices will recognize that once the matrices absorb water their mechanical integrity is modified (i.e. they generally become permanently stiff and warped). They also completely lose their ability to return to their original fluffy state and their ability to absorb water is irreversibly lost. However, collagen matrix can generally be treated the same way as gauze material using aqueous salt solutions.

The methods of the present invention can also be used for devices other than wound care devices. For example, a device comprises a contact lens. Lenses were treated first with silver nitrate solution, briefly rinsed with water and then soaked in a sodium saccharinate solution to form the silver saccharinate complex in the hydrophilic lens matrix. After rinsing the lens were dried in ambient atmosphere. In testing, the treated lenses were found to be antimicrobial.

The present invention comprises catheters having surfaces comprising silver compounds. The catheters can be made of silicon based polymers, polyurethanes, latex based, polyvinyl chloride or other biocompatible polymers. Catheters may or may not possess lubricious surfaces and can be treated to deposit silver, which then can be released in a sustained release fashion from the surface. Catheters having hydrophilic (lubricious) surfaces can be treated in manner similar to gauze materials. The methods of the present invention deposit fine particles of silver saccharinate in the hydrophilic lubricious coating on the catheter. It is to be understood that the use of silver saccharinate is not to be construed as limiting.

In another embodiment, catheters can be made antimicrobial using silver compounds disclosed herein, by coating them with silver containing compositions, See Example 23.

Instead of dipping, coatings may also be applied by spraying the solution or by dispensing solution in patterns from syringes under pressure in commercially available dispensing devices. Coating compositions containing silver compounds may be non-aqueous or aqueous. They may contain mixtures of polymers that may be synthetic or natural. The synthetic polymers may be polyurethane resins, acrylate resins, acetal resins, polyimides, polyamides, polyacarbonates and other known to those skilled in developing and formulating coating compositions. The synthetic polymers may be homopolymers or copolymers and natural polymers may be further chemically modified. Examples of natural polymers are cellulose ethers, rosins, casein and others.

The present invention comprises methods for making hydrocolloid dressings antimicrobial using silver compounds of the present invention. Examples are Flexigel® dressing from commercially available from Smith & Nephew Inc. of Largo, Fla., various hydrogel type sheet products (Aquadapt® hydrogel foam) from Hydromer Inc of New Jersey. Dressings can be in continuous sheet form or strands. In one method, the dressing was hydrated successively with sodium saccharinate solution and silver nitrate solution to precipitate silver saccharinate inside and on the dressing surface. In an alternative method, the silver saccharinate was precipitated in fine particle form in the polymerization mixture and subsequently cross-linked, formed and dehydrated. This method is described in detail in U.S. Pat. No. 6,605,751 which is incorporated herein by reference. Similarly the silver saccharinate can be precipitated in situ during the preparation of Aquadapt® foam. To illustrate the construct of silver containing Aquadapt® foam, silver saccharinate suspension was formed by mixing equal volumes of 0.1M aqueous solutions of silver nitrate and sodium saccharinate to the mixture disclosed in example 5 of U.S. Pat. No. 5,420,197. The amount of silver saccharinate suspension can be controlled depending upon the silver content desired in the finished foam.

In various embodiments disclosed herein, silver compounds are formed in situ for incorporation into medical devices. Silver saccharinate or other silver compounds of the present invention can be added in solid form as dry powder or in many other forms ordinarily known to those skilled in the art. For example, silver compounds of the present invention can be dispersed on physiologically inert supports, and porous filler materials, both inorganic (silicate powders) and organic (silicone microspheres) can be impregnated with silver compounds, that then can be incorporated into different medical devices and dressings following normal production methods. In another method, silver compounds can be encapsulated in micro-particles and then utilized as reservoirs of silver by blending the silver microparticles in lotion and cream formulations. Such an approach may yield a matrix that in addition to providing a silver ion reservoir may also not discolor in response to light and heat. In yet another approach, silver compounds may be deposited by vapor or vacuum deposition techniques similar to those disclosed in U.S. Pat. No. 4,728,323.

Another embodiment of the present invention is an improved hydrocolloid dressing containing silver saccharinate that does not discolor with time. For example, Flexigel® dressings commercially available from Smith & Nephew Inc. of Largo, Fla. after incorporation of silver saccharinate may slowly discolor to brown over time. Such dressing can be improved to resist discoloration by light by hydrating the dressing with hydrogen peroxide. To have the intended effect, the concentration of hydrogen peroxide in the dressing may be between 0.01% and 10.0% and is preferably ≤5.0%.

Another class of dressings that are amenable to antimicrobial treatment using silver compounds is the wet therapy dressing. In wound management, such dressings facilitate the debridement of wounds. The dressing usually is composed of hydrated layer of polyacrylate based cross-linked polymer having high water absorbency that is held in a polypropylene cloth pouch. In rendering the dressing antimicrobial using the methods of the present invention, TenderWet® Active dressing (4"×4") was first wet with a pre-formed suspension of silver saccharinate followed by the addition of Ringer's solution (an aqueous mixture of sodium chloride, potassium chloride and calcium chloride). The total amount of liquids added per dressing was approximately 30 gm and the amount of silver in the liquids was varied between 0.007% w/w to 1% w/w with preferred amount of silver between 0.01% and 0.025%. By maintaining at least 0.01% w/w of silver in the soaking liquids, antimicrobial activity was sustained for over 3 days. Following steam sterilization under 122° C. for over 90 minutes, the dressing with silver saccharinate showed no discoloration. Continuous light exposure for 24 h also did not cause any graying of the dressing. In contrast, the dressing made with silver chloride at the same silver content discolored after sterilization step and also after light exposure.

Medical devices in the form of silver containing adhesive films having antimicrobial activity can be formed using silver compounds of the present invention. One embodiment comprises a laminated construct of polyurethane film having an adhesive layer containing antimicrobial silver. An example of such construct without silver is an OpSite® dressing commercially available from Smith and Nephew. By incorporating silver saccharinate in the adhesive and depositing the adhesive on the polyurethane layer, one can impart antimicrobial activity to the film construct. When used to cover incision sites or IV sites, such constructs can potentially reduce infection related incidents after surgery. Such constructs are transparent and non-discoloring due to the presence of more light stable silver can allow for inspection of wounds or any reddening of underlying skin. This would be a significant advance over the prior art where the silver containing adhesive films are not white but brown in color (Arglaes® silver film from Medline Industries, Mundelein, Ill.). See Example AD24.

Antimicrobial Compositions

Compositions of the present invention comprise the silver compounds taught herein. Composition comprise a suspension of the silver compound in an aqueous or nonaqueous solution, or can be a mixture or admixture of the silver compound in a formulation that is generally known for treatment of skin, dermal, topical, covering, or other surfaces treatments. The present invention comprises compositions comprising creams and lotions, gels, ointments, pessaries, impregnated inorganic and organic carriers, and coatings (aqueous and non-aqueous). Compositions may be used in treating minor infections of skins, acute and chronic wounds, pressure sores, burns, burn wounds and ulcers, other skin lesions, infections of mucous membranes and other infections or maladies caused by bacteria, viruses, yeasts, fungi, molds, mildew, protozoa and microbes. The antimicrobial property can be imparted to cosmetics products such as skin wraps, compresses for acne and blemishes, scar reduction, tattoo removal and laser resurfacing; to personal and skin care products such as hand creams or lotions, conditioners, barrier creams, lubricating preparations. Compositions comprising said silver compounds may be also used to treatment wounds of all types in animals and in control of infection in animals.

The methods of preparation of compositions such as creams and lotions are well known in the literature. An antimicrobial cream comprising silver saccharinate was prepared and is taught in Example AD25. In general, to a pre-made dermal cream base, appropriate amounts of a sodium saccharinate solution and a silver nitrate solutions were added and blended to form an in situ silver saccharinate precipitate. To a petrolatum base, a preformed suspension of silver saccharinate was added and mixed to uniformity. When compared to similar creams made with silver chloride, the compositions of the present invention were not only antimicrobial but also resisted light discoloration for a longer period of time. Antimicrobial creams, lotions and ointments prepared from oil/water and water/oil emulsions and petrolatum base are also contemplated by the present invention. The antimicrobial compositions of the inventions are not limited to non-aqueous creams or lotions, but can also be prepared as amorphous aqueous gel.

A variety of cellulose derivatives may be used in formulating gels into which silver compounds of the present invention can be incorporated. Examples are cellulose derivatives from Dow Chemical and Hercules Inc sold under Methocel®, Natrasol®, and Aqualon® brands. Antimicrobial gel compositions comprising natural polymers or gum such as xanthan gum, guar gum, carageenan, locust bean gum, pectin, alginates, gellan gum or their mixtures with other water soluble polymers are also contemplated by the present invention. Gels may also contain multiple silver compounds or may contain active agents in addition to one or more silver compounds. Additives such as surfactants, emulsifiers, emollients, colorants, humectants, oxidizing agents, pH adjusting agents to promote galvanic reaction with silver may also be present in gel compositions. Gels in which antimicrobial activity is a concomitant property and not the main functionality are encompassed by the present invention.

Gels may comprise synthetic homopolymers and copolymers formed using acrylic acid, methacrylic acid and their sodium salts, acrylamide, methacrylamide, acrylamide or methacrylamide with alkyl substituents on nitrogen, hydroxyalkyl acrylates, maleic anhydride, vinyl pyrrolidone, vinyl 2-ethyl oxazoline, methyl vinyl ether. These polymers are commercially available from a variety of sources.

Gel compositions exhibiting sustained release of antimicrobial silver compounds of the present invention may comprise varying amounts of the said compounds depending on the end use. For minor cuts and wounds, daily application of gels may be needed thus requiring only small amounts of silver. Hand sanitizing gels also may comprise of only a small amount of silver, from 100 ppm to 500 ppm based on gel weight. On the other hand in situations where wound bandages are changed every few days, gels having a greater amount of silver are required to maintain antimicrobial levels in the wound site. The amount of silver compounds can vary from 10 ppm to 50,000 ppm and from between 50 ppm and 20,000 ppm and values ranging between 500 ppm and 10000 ppm, based on gel weight.

Adhesives compositions having antimicrobial activity for use in skin bandages and other similar bandages may contain silver compounds of the present invention in dispersed form in the adhesive. In one embodiment, silver containing adhesive was compounded as follows. To an adhesive in a non-aqueous solvent, stabilized silver saccharinate suspension was added and mixed to uniformity and a thin film of adhesive mixture was applied on polyurethane film and dried to remove the solvent and finally covered with release liner. See Example 24. Other methods commonly known in the art can be employed to prepare an adhesive composition and laminated film construct, without departing from the scope of the invention. The class of adhesives is generally not important to formulating the adhesive composition. However, base adhesives that are biocompatible and have a low glass transition temperature such as, polyacrylates (crosslinked or linear) and polyurethanes are contemplated. However base adhesive compositions are not limited to synthetic polymers. Natural polymers such as casein or starch can also be used in formulating silver containing adhesive compositions. Other ingredients may be added to improve characteristics of the adhesive compositions without affecting the antimicrobial property. For instance, humectants such as glycerol, propylene glycol may be added to increase water retention. Stabilizers such as copper chloride or other cupric salts, citrate, or lactate may be added for improving stability against light discoloration. Surfactants may be added to increase the stability of the composition and preventingredients from separating out. The amount of silver in adhesive compositions comprising silver compounds of the present invention is typically between 10 ppm and 50000 ppm or a range between 500 ppm and 20000 ppm or a range between 1000 ppm and 10000 ppm.

Antimicrobial formulations for the application to devices may be aqueous or non-aqueous, and where such formulations are used to coat devices or surfaces are referred to herein as coatings. An aqueous composition may be made of any water soluble polymer wherein any of the silver compounds disclosed may be dispersed or formed in situ. Besides the polymeric component, other ingredients may be added to for stability, dispersibility, compatibility wet lubricity, and improving plasticity. Ingredients that are self cross-linkable or cross-link with other components may be present. The resulting dry coating, while improving wet lubricity, can be hydrated in water (moist or humid air environment) but is incapable of self dissolution and can act as the reservoir for silver for slow sustained release for persistent antimicrobial action on the surface.

Coatings comprising non-aqueous solvents and silver compounds are also contemplated by the present invention. Such coatings may offer the advantage of drying quickly after application. Often such coating compositions comprise a polymeric ingredient that may possess some affinity for water. After application, the dried coating may be able to absorb enough water from the ambient atmosphere to maintain an inhibitory level of silver ions to prevent growth of microbes on the surfaces. Such coating compositions may be useful to coat inside of HVAC ducts, shower curtains, surgery room drapes or simply sprayed as a mist wherever one wants to leave an antimicrobial coat to prevent microbial growth. For example, such coating compositions may be well suited in the preparation of antimicrobial contact lens cases. Coating compositions of the present invention do not necessary have to contain polymeric ingredient. Compositions may simply be in form of a stabilized suspension that may be sprayed in the form of mist and wiped down e.g. on table tops, medical lab benches, surgery room carts to make surfaces germ free.

Dental or oral hygiene compositions comprising silver compounds of the present invention are contemplated. Dental compositions include temporary dental cements, fillings and adhesives or bases for holding dentures in place. Oral hygiene compositions in the prevention and control of bad breath may include the silver compounds of the present invention. Those ordinarily skilled in the art will readily recognize that the amount of silver must be optimized to meet the specific requirement of each application in the dental compositions and products. Preferred amount of silver in the dental or oral hygiene compositions of the present invention is below 50000 ppm.

Silver compounds of the present invention may also be used in variety of household products. Gels for bathroom use, mops for floor cleaning, scouring pads may be incorporated with silver compounds and rendered antimicrobial.

Other compositions that may utilize silver compounds of the present invention are aqueous ink compositions. Inks may be dye based or stabilized pigment based. More specifically, the ink compositions that are used in drop on demand ink jet printers such Epson Stylus® and HP Desk Jet® series printers. Silver compounds can readily provide sufficient antimicrobial activity to prevent fungi and bacteria from growing and improving ink cartridge shelf life.

In general, the present invention comprises antimicrobial medical devices comprising an article comprising, at least one surface contacted by a composition comprising a silver, zinc, or copper compound, wherein the article is resistant to discoloration by heat and light. The invention also contemplates contacting surfaces and rendering surfaces, where ever the surfaces are found, and not limited to surfaces of medical devices, antimicrobial, by which is meant that once treated with the compounds taught herein, the surfaces provide silver, copper or zinc that will kill, or impede the growth of microorganisms. The articles may be fibrous, woven or nonwoven, a hydrophilic matrix device, comprising cellulose ether derivatives, hydroxyl alkyl cellulose ether derivatives, hydroxyl alkyl cellulose derivatives or mixtures thereof, or a matrix device of cotton, rayon, acrylics, acetate fibers, alginates and other synthetic and natural polymers or blends; moisture containing wound dressings, monitor leads, wound dressings, hydrated plastic implants, hydrocolloid dressings, dressings used in wet therapy, super-absorbent foams, hydrophilic polyurethane foams, activated charcoal dressings, compresses, xeroform petrolatum dressings, venous, urinary and pain management system catheters, stents, guidewires, shunts, cannulae, catheter adapters or other solid or hollow tubular devices, tracheal tubes, contact lens cases, nebulizers, sutures, incontinence products; feminine hygiene products, ostomy pouches; ostomy plugs, respiratory appliances, feeding appliances, contact lenses, hearing aids, haemostats, or urine or waste collection bags. The articles may be of any material to which the compositions can be affixed, woven cotton gauzes, and other woven and nonwoven materials like polyesters, rayon, acetate, nylon and nylon blends with cotton of one to ten ply. The composition further comprises at least one active agent or additive. The active agents comprise antimicrobial agents, antifungal agents, antiviral agents, growth factors, angiogenic factors, anaesthetics, mucopolysaccharides and wound healing proteins. The antimicrobial agents comprise isoniazid, ethambutol, pyrazinamide, streptomycin, clofazimine, rifabutin, fluoroquinolones, ofloxacin, sparfloxacin, rifamin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclarazil, acyclovir, trifluorouridine, foscarnet, penicillin, gentamicin, ganciclovir, iatroconazole, miconazole, zinc-pyrithione, heavy metals including but not limited to platinum or gold, and their combined forms including salts such as halides, saccharinates and complexes with carriers and other forms, or nanoparticles of silver, zinc and copper. Such nanoparticles and uses thereof are taught in copending application, U.S. application Ser. No. 11/194, 951, filed Aug. 1, 2005, and PCT/US2005/027261, filed Aug. 1, 2005, incorporated herein by reference in their entireties. The compositions comprise the silver compounds taught herein. The present invention also comprises compositions comprising a silver, zinc, or copper compound, wherein the composition is resistant to discoloration by heat and light. The composition further comprises suspensions, lotions and creams, ointments, jellies, gels, pessaries, inorganic carriers, porous glasses, oxides, silicates, talc, mica, silica, titania, zirconia, insoluble polymeric microspheres, hydroxy apatite, cellulose powder, chitin, chitosan, cross-linked polymers or topical gels. The composition further comprises at least one active agent or additive, which may comprise antimicrobial agents, antifungal agents, antiviral agents, growth factors, angiogenic factors, anaesthetics, mucopolysaccharides and wound healing proteins, wherein the antimicrobial agents comprise isoniazid, ethambutol, pyrazinamide, streptomycin, clofazimine, rifabutin, fluoroquinolones, ofloxacin, sparfloxacin, rifamin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclarazil, acyclovir, trifluorouridine, foscarnet, penicillin, gentamicin, ganciclovir, iatroconazole, miconazole, zinc-pyrithione, heavy metals including but not limited to platinum or gold, and their combined forms including salts such as halides, saccharinates and complexes with carriers and other forms, or nanoparticles of silver, zinc and copper. The compositions comprise the silver compounds taught herein. The methods of the present invention also comprise methods of making the devices and compositions taught herein and methods of an animal, including humans and animals, that with a condition caused by microbial agents, comprising, applying a composition or device comprising a silver compound, wherein the composition or device is resistant to discoloration due to heat or light.

The term "light stable" in the present context is meant to indicate either of two conditions; (i) no visible change in the color of the compositions of patient and wound care products after 24 hour exposure to light conditions typically encountered indoors in hospital, offices, or home that are normally used to aid visibility. The term "heat stable" in the present context is meant to indicate antimicrobial devices and compositions comprising the silver compounds would be able to withstand steam sterilization for 122° C. for 15 minutes without evidence of degradation of activity or color.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1 Cotton Gauze

Cotton gauze with silver was prepared as follows: Sodium saccharinate (0.205 gm) was dissolved in 10 ml de-ionized water to which 1 ml of silver nitrate (1M) was added to form silver saccharinate precipitate. 2 ml of suspension was diluted with 3 ml of water and evenly spread on 2"×2" cotton gauze (Curity brand from The Kendall Company, Mansfield, Mass.). The gauze was blotted to remove excess liquid and dried in oven at 40-45° C.

A. 3"×3" cotton gauze (Curity brand from The Kendall Company, Mansfield, Mass.) was dipped in 10-12 ml of 0.1M silver nitrate solution. It was blotted on paper and dipped in 15 to 20 ml of 0.125 M sodium saccharin to precipitate silver saccharinate in and on the cotton fibers, blotted and dried at 70° C. for 0.5 h.

B. Gauze was made by the same procedure as in example 1A except it was dried in oven at 135° C. for 12 minutes.

C. Gauze was made by the procedure of Example 1A, except it was dried at 135° C. for 30 minutes.

D. Gauze material (3"×3" Curity brand) was soaked in silver saccharinate suspension that was prepared by mixing equal volumes (5 ml) of silver nitrate and sodium saccharinate solutions of varying molarities; (0.1 M (high), 0.05 M (medium) and 0.02 M (low) for silver salt and 0.125 M, 0.0625 and 0.025 M for sodium salt, blotted and dried at 45° C.

E. Gauze was prepared following the procedure of D except a surfactant Tween 20 at 0.5% w/w was present in the final soak solution with silver nitrate and sodium saccharinate concentrations at 0.1 M and 0.125 M respectively. The resulting silver impregnated gauze was dried at 135° C. for 7-8 minutes.

F. Improved light stability. Two 2"×2" pieces of cotton gauze (Bulkee brand, Medline Industries, Mundelein, Ill.) were soaked in a silver saccharinate suspension, prepared by mixing 15 ml each of 0.1 M silver nitrate and 0.125 M sodium saccharinate, for a minute, blotted and then dipped in 12 ml of 0.125M sodium saccharinate solution containing 5% hydrogen peroxide and quickly removed. The gauze was dried in oven at 135° C. for 12 minutes.

G. The second gauze piece in F was dried at 135° C. for 5 minutes.

H. A 5.5 ml solution of sodium saccharinate (0.125 M) and Tween 20 (0.05 g) was prepared, to which was added 5.5 ml silver nitrate solution (0.1 M). Separately a mixture of sodium saccharinate (11 ml, 0.125 M) and 30% hydrogen peroxide (1 ml) was prepared and set aside. A pair of gauze pieces 2"×2" of Bulkee gauze material were soaked in a silver saccharinate suspension, blotted and dipped in the peroxide/saccharinate solution. If blotted properly, no loss of particulate matter from the gauze occurred. After peroxide dip, the gauzes were blotted and dried in oven at 135° C. for 10-12 mins.

I. A pair of gauze pieces (2"×2") were made, identical to H, except the hydrogen peroxide concentration was 1% instead of 3% in the soak solution.

Example 2 Alginate Fiber Dressing 1 ml of silver saccharinate suspension prepared in Example 1 was diluted with 10 ml denatured ethanol to give a hazy solution. A 2"×4" piece of alginate/CMC fiber dressing (Maxsorb brand, Medline Industries, Mundelein, Ill.) was soaked in the solution, gently blotted and dried in oven at 45° C. The resulting dressing was antimicrobial.

Example 3 Drain Sponge

A drain sponge made of polyester and rayon (Avant brand, Medline Industries, Mundelein, Ill.) was soaked for 1-2 minutes in 30 ml silver nitrate solution (0.04 M) under ambient light, blotted with paper and then quickly soaked in sodium saccharinate solution (0.05 M) for 1-2 minutes. The sponge was blotted to squeeze out excess fluid, dried at 45° C. overnight to yield a slightly cream colored silver containing product.

Example 4 Stretchable Bandage

A stretchable bandage made from polyester (Softform brand, Medline Industries, Mundelein, Ill.) was impregnated with silver saccharinate salt following the procedure of Example 3.

4A. Cotton gauze. Barbituric acid (0.184 g) and anhydrous sodium carbonate (0.1505 g) were added to de-ionized water (10 ml) and stirred to give a clear solution. Silver nitrate (1 ml, 1 M) was added to precipitate silver barbiturate and form a suspension. Gauze piece (Curity brand) measuring 2"×2" was immersed in the suspension for 1-2 minutes, blotted and dried at 45° C.

Example 5 Alginate Fiber Dressing

The dressing with silver saccharinate was made by changing reagent concentrations. A 4"×4" dressing was immersed in 30 ml silver nitrate solution (0.01 M, 50% v/v ethanol/water) for 1 min, blotted and immersed in 60 ml sodium saccharinate solution (0.016 M, 67% ethanol/water) for few minutes. Excess fluid from the dressing was removed and upon drying for 1-2 h at 45° C., resulted in a silver containing dressing.

Example 6 Gel sheet

A small of piece (1"×1") hydrogel sheet (Flexigel brand, Acrymed Inc., Tigard, Oreg.) was hydrated with 0.1 ml silver nitrate (0.1 M). After few minutes to allow for the liquid to diffuse into the gel matrix, 0.1 ml of sodium saccharinate (0.125 M) was spread over the gel piece. Due to the formation of insoluble silver saccharinate, the gel piece turned opaque white. After few days the gel piece changed color from opaque white to red brown.

6A. Gel sheet. A small of piece (1"×1") hydrogel sheet (Flexigel) was hydrated with 0.2 ml sodium saccharinate (0.125 M) containing 3% w/w hydrogen peroxide. After few minutes to allow for the liquid to diffuse into the gel matrix, 0.2 ml of silver nitrate (0.1 M) was spread over the gel piece and allowed to be absorbed. Due to the formation of insoluble silver saccharinate, the gel piece turned opaque white. After 24 h continuous lab light exposure the opaque white coloration of gel sheet was unchanged.

Example 7 Collagen Sheet

A 4"×2.5" piece of collagen matrix sheet (piece) (Integra Life Sciences, NJ) was rinsed three times (15 ml×3) with 70% v/v isopropyl alcohol (IPA)/$H_2O$ to remove the buffer solution in which it was stored, blotted with paper and placed in petri-dish. 15 ml of silver nitrate (0.1M) solution was evenly poured over the piece and allowed to soak in for 2-3 minutes. The piece was blotted and transferred to second petri-dish and 15 ml of 0.125M sodium saccharinate solution was poured on it. After soaking for 15 minutes, the piece was blotted, rinsed twice (20 ml×2) with 51% v/v IPA/$H_2O$ and stored in another dish containing freshly made phosphate buffered saline (PBS) solution.

Example 8 Chitosan Powder

In a cup, chitosan powder (0.5 g), IPA (2 ml) and de-ionized water (18 ml) were mixed and stirred. In a test tube, silver saccharinate was precipitated by successively adding sodium saccharinate (1 ml, 0.125 M) and silver nitrate (1 ml, 0.1 M). The silver saccharinate suspension was dripped into the stirred suspension of chitosan powder. After completing addition of silver saccharinate, the chitosan powder suspension was stirred for 0.5 h and then filtered. The filtered solids were washed with 100 ml of water and dried overnight in oven at 45° C.

Example 9 Ointment

In a test tube, Tween 20 (0.05 g) was weighed and dissolved in de-ionized water (0.25 ml). Sodium saccharinate (0.45 ml, 1M) solution was added to a test tube followed by silver nitrate (0.355 ml, 1M) to form silver saccharinate. The test tube contents were added to 12 g of petrolatum base (Plastibase brand, Mike's Pharmacy, Vancouver, Wash.) in a cup and vigorously mixed to a uniform cream with slight white opacity. No color change due to 24 h continuous lab light exposure was observed.

Example 10 Ointment Using Water in Oil (w/o) Base

The silver containing cream was prepared exactly as in example 9 except the ointment base was a w/o base (Dermabase brand, Mike's Pharmacy, Vancouver, Wash.). With respect to 24 h lab light exposure results similar to example 9 were observed.

Example 11 Talc Powder

Talc powder (3 g) was dispersed in IPA/water mixture (5 ml/30 ml). Sodium saccharinate solution (0.06 g/5 ml) in water was added to the stirred suspension. Silver nitrate (0.25 ml, 1 M) was added drop wise to the stirred mixture to precipitate silver saccharinate. The suspension was stirred for 15 minutes. Talc powder with dispersed silver saccharinate was recovered after filtering and drying at 60-65° C.

Example 12 Cotton Gauze

The method of example 1A was modified. 1 foot long cotton gauze (Bulkee brand, Medline Industries, Mundelein, Ill.) was dipped in a suspension of silver saccharinate prepared by mixing 60 ml of 0.1 M silver nitrate solution and 60 ml 0.125 M sodium saccharin, blotted and dried at 110° C. for 12 minutes.

Example 13 Drain Sponge

A pair of drain sponges (Avant brand, Medline Industries, Mundelein, Ill.) was soaked for 1-2 minutes in a suspension of silver saccharinate prepared from 30 ml silver nitrate solution (0.1 M) and 30 ml sodium saccharinate solution (0.125 M). Sponges were blotted to squeeze out excess fluid, dried at 110° C. for 12 minutes to yield slightly cream colored silver containing prototypes.

Example 14 Antimicrobial Efficacy of Devices and Compositions of Present Invention The antimicrobial activity of the devices and compositions made in the Examples above was verified by standard zone of inhibition microbiology assay using *Staphyloccocus aureus* bacteria. Disks of 5-7 mm size were cut from treated and untreated gauze and placed on a Mueller Hinton Agar (MHA) plate that was inoculated with bacteria and incubated overnight at 37° C. Treated gauze samples with silver ions showed a clear zone of inhibition around it. Untreated gauze and Silvasorb served as negative and positive control, respectively. Other antimicrobial devices were prepared using silver saccharinate. The results from zone of inhibition assay on prepared devices are presented in Table 5. Antimicrobial activity is consistently seen in diverse substrates such as simple cotton gauze, synthetic polymer foam products or collagen sheet.

To verify sustained release of silver from different substrates a serial time transfer test was carried out. The same test gauze disks were transferred to a freshly inoculated MHA plate each day and corresponding zones of inhibition from each successive transfer were measured until there was no activity. From the results presented in Table 6 sustained release of effective amounts of silver for 3 to 7 days is seen depending on silver concentration. Release up to as much as 14 days is observed for collagen sheet demonstrating an important aspect of the present invention. Similar sustained release activity lasting about 7 days against gram negative bacteria *Pseudomonas aeruginosa* is also seen (Table 7).

Several substrates were also tested for broad-based activity against a set of microbes including gram positive, gram negative, yeast and fungi. In all cases silver saccharinate containing substrates were active (Table 8).

The thermal and light discoloration resistance of various gauzes prepared using silver saccharinate can be assessed from the results in Table 9. The thermal resistance is important because often these products undergo drying steps in manufacturing where they are exposed to higher temperatures. In addition to thermal resistance, resistance to discoloration is not only important for aesthetic reasons but also for allowing the packaging operations a time interval to operate without having to take special measures to protect from light. A 24 h time window could be considered reasonable for packaging operations. The results show that various gauze samples impregnated with silver saccharinate are not discolored after 24 h light exposure. In contrast the samples made identically but with silver chloride are badly discolored. Further, gauze subjected to 135° C. for 12 minutes did not discolor even after additional 24 h exposure (total 48 h). Some of the substrates made with silver saccharinate as active ingredient were tested for cytotoxicity using agarose overlay test. The results indicated that samples with <0.8% wt silver based on sample weight were non-toxic. All of the samples listed in the tables have silver content below the toxic limit and are also quite antimicrobial.

TABLE 5

24 h ZOI Assay Against *Staphylococcus aureus*

| Example | Substrate | ZOI |
|---|---|---|
| 1 | Cotton gauze | 13/6.5 |
| 1D high Ag | Cotton gauze | 11.5/7 |
| 1D med. Ag | Cotton gauze | 12/7 |
| 1D low Ag | Cotton gauze | 10/7 |
| 2 | Alginate dressing | 13/6.5 |
| 3 | Polyester/Rayon woven sponge | 13/6.5 |
| 4 | Polyester woven roll | 7/4 |
| 4A | Cotton gauze | 13.5/6.5 |
| Control | Untreated gauze | 6.5/6.5 |
| 5 | Alginate dressing | 9.5/6.5 |
| 6 | Hydrogel sheet | 10/6 |
| 6A | Hydrogel sheet | 25/9 |
| 7 | Collagen sheet | 12/6 |
| 8 | Chitosan powder | 13.5/6.5 |
| 9 | O/W cream base | 4.5/2 |
| 10 | W/O cream base | 4/2.5 |
| 11 | Talc powder | 13.5/6.5 |
| Control | Silvasorb gel sheet | 13.5/7 |

TABLE 6

ZOI Serial Transfer Data against *Staphylococcus Aureus* (Day 1 to Day 14)

| Exam. | SUB | 1* | 2* | 3* | 4* | 5* | 6* | 7* |
|---|---|---|---|---|---|---|---|---|
| 1 | A | 13.5/6.5 | 15/7 | 9.5/7 | 14/7 | Not detd. | 9.5/6.5 | Stopped |
| 1D High Ag | A | 14/7 | 14/7 | 11/7 | 10/7 | 8/7 | 8/7 | 8/7 |
| 1D Med Ag | A | 12/7 | 10.5/6 | 7/6 | 6/6 | — | — | — |
| 1D Low Ag | A | 10/7 | 7.5/6.5 | 6.5/6.5 | — | — | — | — |
| 2 | B | 13/6.5 | 10/6.5 | 7/6.5 | 6.5/6.5 | — | — | — |
| 7 | C | 12/6 | 12/5.5 | 11/5 | 8/5.5 | 11/5.5 | 8.5/5.5 | 8/5.5 |

| | | Day 8 | Day 9 | Day 10 | Day 11 | Day 12 | Day 13 | Day 14 |
|---|---|---|---|---|---|---|---|---|
| 7 | C | 8/5.5 | 8/5.5 | 7.5/5.5 | 9/5.5 | 8.5/5.5 | 7.5/5.5 | 7.5/6.5 Stopped |

*Day, SUB = Substrate, A = Cotton gauze, B = Alginate dressing, C = Collagen sheet

TABLE 7

ZOI Serial Transfer Data against *Pseudomonas Aeruginosa*

| Exam. | SUB | 1* | 2* | 3* | 4* | 5* | 6* | 7* |
|---|---|---|---|---|---|---|---|---|
| 1D High Ag | A | 11.5/6.5 | 29.5/6.5 | 19.5/6.5 | 31.5/6.5 | 15/6.5 | 9.5/6.5 | 6.5/6.5 |
| 1D Med Ag | A | 10/6.5 | 30.5/6.5 | 17.5/6.5 | 11.5/6.5 | 7/6.5 | 6.5/6.5 | — |

TABLE 7-continued

ZOI Serial Transfer Data against *Pseudomonas Aeruginosa*

| Exam. | SUB | 1* | 2* | 3* | 4* | 5* | 6* | 7* |
|---|---|---|---|---|---|---|---|---|
| 1D Low Ag | A | 8.5/6.5 | 24.5/6.5 | 17.5/6.5 | 10/6.5 | 7/6.5 | 6.5/6.5 | — |
| 7 | C | 10/6 | 10/6 | 14/5.5 | 9.5/5.5 | 8.5/5.5 | 6.5/5.5 | 5.5/5.5 |

*Day, SUB = Substrate, A= Cotton gauze, B = Alginate dressing, C = Collagen sheet

TABLE 8

24 h ZOI Assay of Silver Containing Substrates Against Common Microbes

| Example | *Escheria coli* ATCC 8739 | *Staphylococcus Aureus* ATCC 6538 | *Pseudomonas Aeruginosa* ATCC 9027 | *Candida Albicans* ATCC 10231 | *Aspergillus Niger* ATCC 16404 |
|---|---|---|---|---|---|
| 7 | 8/6 | 12/6 | 9/6 | 10/6 | 16/6 |
| 12 | 11/7 | 14/7 | 12/7 | 14/7 | 18/7 |
| 13 | 11/7 | 15/7 | 12/7 | 15/7 | 19/7 |

TABLE 9

Thermal and Light Stability Test Results

| Example | Substrate | Drying Conditions | Color immediately after drying | Color change after 24 h lab light exposure |
|---|---|---|---|---|
| 1A | Gauze | 70° C./30 min | White | No discoloration |
| 1B | Gauze | 135° C./12 min | White | No discoloration |
| 1C | Gauze | 135° C./30 min | Pale yellow | — |
| 1E | Gauze | 135° C./8 min | White | — |
| 1F | Gauze | 135° C./5 min | White | No discoloration |
| 1G | Gauze | 135° C./12 min | White | No discoloration |
| 1H | Gauze | 135° C./10 min | White | No discoloration |
| 1I | Gauze | 135° C./10 min | White | No discoloration |
| 2 | Alginate dressing | 45° C./1-2 h | Cream (same as original) | No discoloration |
| 6A | Hydrogel sheet | — | — | No discoloration |

Example 15 Hydrophilic Medical Grade PU Foam (0022-01)

Four (1"×1") pieces of 1.6 mm thick polyurethane (PU) foam (Medical grade 562-6) from Rynel Corporation of Boothbay, Me. were soaked in silver saccharinate suspension. To prepare the suspension, Tween 20 (0.05 g) and hydrogen peroxide (0.5 mL, 30%) were added to the sodium saccharinate (5.5 mL, 0.125M) solution, followed by silver nitrate (5.5 mL, 0.1M). After mixing few minutes on vortex mixer, the suspension was poured on four foam pieces laid out in a 6" petri-dish and allowed to soak for a brief period. After blotting away excess liquid with paper, the foam samples were dried at 45 C for 0.5 h. The samples left out on bench for 24 h ambient light exposure and observed for color change. The exposed sample discolored to purple black but those protected from light were unchanged and in all respect identical to untreated foam. The silver treated foam was found to be antimicrobial and showed sustained ionic silver release.

An assortment of PU foam samples from Lendell Manufacturing Company of St. Charles, Mich. were impregnated with silver saccharinate in a similar fashion. Each foam sample was antimicrobial against *Staphylococcus aureus* strain. Upon light exposure, the silver impregnated foams became discolored turning light rust colored, purple black and ash grey. Unexposed silver impregnated foam samples did not discolor and in color were no different from the untreated foam.

Example 16 Gauze Impregnated with Silver-Heterocyclic Compound Complexes

Two 2"×2" Bulkee II six ply cotton gauzes were successively soaked in aqueous silver nitrate (0.1M) and ethanol solution of benzotriazole (0.06M), blotted dry with paper and dried in oven at 45 C for 0.5 h. Similarly, another pair of cotton gauze pieces was treated but using silve-bezimidazole complex.

Both samples (one of each kind) were exposed to ambient light for 72 h. No discernable discoloration between exposed and unexposed samples was observed. Both samples showed antimicrobial activity against *Staphylococcus aureus* that sustained over 4 days.

Example 17 Aqueous Gel Prototype

A syringe filled with aqueous gel (KY jelly) (Bard Inc) was emptied to yield 8 gm of gel. In a cup silver saccharinate was prepared by mixing 40 µL of sodium saccharinate (0.125M) and 50 µL silver nitrate (0.1M) to which 3.3 µL of 30% hydrogen peroxide was added. Silver saccharinate suspension and gel were mixed to uniformity. Syringe was refilled with gel and exposed to ambient light for 24 h. Very faint discoloration was observed.

Example 18 Aqueous Gel Prototype

The test in Example 17 was repeated except using 25 µL each of sodium saccharinate and silver nitrate and hydrogen peroxide was substituted with 25 µL 0.8M sodium chloride. The resulting gel in syringe showed no discoloration after 24 h of continuous lab light exposure.

Example 19 Solubility of Silver Saccharinate in Water at Approximately 25° C.

An aqueous saturated solution of silver saccharinate was prepared according to the procedure disclosed in published US patent application no. US2003/0186955. The solution was analyzed for silver using AAS/ICP. From the analysis, the silver saccharinate solubility in water was found to be 3.5 mg/L.

Example 20 Aqueous Gel with Silver Saccharinate

Hydroxyethyl Cellulose (Spectrum Chemical Co.) (0.4 g) was dissolved in 12 mL of warm deionized water. Glycerol (2 g) was mixed in the viscous mass. In a test tube, silver saccharinate suspension was prepared by mixing Tween 20 (16.7 g/L, 1 mL), sodium saccharinate (0.125M, 1 mL) and silver nitrate (0.1M, 1 mL) and hydrogen peroxide (30%, 0.6 mL). The suspension was mixed with the viscous mass to form a slightly white opaque gel. After 24 h light exposure, the gel color had turned very faint blue but acceptable. Unexposed sample color was unchanged.

Example 21 Aqueous Gel with Silver-Benzotriazole Complex

Hydroxyethyl Cellulose (Spectrum Chemical Co.) (0.4 g) was dissolved in 12 mL of warm deionized water. Glycerol (2 g) was mixed in the viscous mass. In a test tube, silver benotriazole complex was prepared by dissolving benzotriazole (0.012 g) in ethanol (0.25 mL) and silver nitrate (0.1M, 1 mL) to it. The resulting white suspension was mixed with the viscous mass to form a slightly white opaque gel. After 24 h light exposure, the gel color had turned very faint pink but acceptable. Unexposed sample color was unchanged.

Example 22 Silicone Catheter Impregnated with Silver Saccharinate

Saccharin (—NH form, 0.05-0.06 mg) was dissolved in tetrahydrofuran (THF) (5 mL) in a test tube. A pre-cleaned 4" long 14 Fr silicone catheter stem (Degania Ltd., Israel) was dipped in the THF solution for 0.5 h at room temperature. Then it was transferred without rinsing to another test tube containing silver nitrate solution (mixture of 3M aqueous solution (3 mL) and 70% aqueous isopropanol (3 mL)) and soaked for 0.5 h. It was rinsed with water and dried in oven at 135° C. for 5-7 minutes. Catheter sample was found to be antimicrobial against *Staphyloccus aureus* in ZOI assay. This method is generally suitable for catheters formed using cross-linked polymers, such as silicones, polyurethanes and many others.

Example 23 Silicone Catheter Coated with Coating Comprising Silver Saccharinate A coating mixture was first prepared as follows. A 1:1 mixture of two part silicone resin (LSR-A (1.2 g) and LSR-B (1.2 g), Degania Silicone Ltd., Israel) was mixed and then diluted with toluene (5 mL). Separately appropriate amounts of saccharin (0.25 g) and silver nitrate (0.25 g) were dissolved in THF (5 mL) and 85% v/v acetone-water mixture (3 mL) respectively and mixed to form silver saccharinate as fine precipitate. The suspension was poured in the silicone solution of toluene and mixed to uniformity. Catheter stems (4" long, 14 Fr) were dipped in the silver containing silicone resin solution to an even coat, dried to remove solvent (1 h at 25° C., 1 h at 75° C. and 16 h at 125° C.) and cured. The catheter was found to be active against *Staphyloccus aureus* in ZOI assay.

Example 24 Silver Saccharinate Comprising Adhesive Formulation

Polyvinyl pyrrolidone (Sigma, MW 40K) solution in 70% aqueous isopropanol was prepared (0.3 g/5 mL). To this solution glycerol (1.5 g) was added, mixed and set aside. To the PVP-glycerol mixture (0.7 g), sodium saccharinate aqueous stock solution (0.25 ml, 1M) was added and vortexed, followed by silver nitrate aqueous stock solution (0.25 mL, 1M). The resulting milky mixture (0.7 g) was added to a polyurethane base adhesive (7 g, Durotak 380-2819) from Intelicoat Technologies of UK and mixed to uniformity. Using a #10 Meyer rod an adhesive film was prepared on a polypropylene plastic film. The adhesive film did not undergo color change with heat over 2 weeks at 45° C.

What is claimed is:

1. An antimicrobial medical device, comprising at least one surface contacted by a composition comprising silver saccharinate, wherein the at least one surface is resistant to discoloration by heat and light, wherein the molar ratio of saccharinate to silver is between 1 and 1.5, and wherein the silver saccharinate is a compound formed from a chemical reaction between a silver salt and a saccharinate salt.

2. The device of claim 1, wherein the device comprises a hydrophilic matrix device, comprising cellulose ether derivatives, hydroxyl alkyl cellulose ether derivatives, hydroxyl alkyl cellulose derivatives or mixtures thereof; a matrix device of cotton, rayon, acrylics, acetate fibers, alginates or other synthetic or natural polymers or blends; a moisture containing wound dressings; a monitor lead; a wound dressing; a hydrated plastic implant; a hydrocolloid dressing; a dressing used in wet therapy; a superabsorbent foam; a hydrophilic polyurethane foam; an activated charcoal dressing; a compress; a xeroform petrolatum dressing; a venous, urinary or pain management system catheter; a stent; a guidewire; a shunt; a cannulae; a catheter adapter or other solid or hollow tubular device; a tracheal tube; a contact lens case; a nebulizer; sutures; an incontinence product; a feminine hygiene product; an ostomy pouch; an ostomy plug; a respiratory appliance; a feeding appliance; a contact lens; a hearing aid; a haemostat; or a urine or waste collection bag.

3. The device of claim 1, wherein the device comprises woven cotton gauzes.

4. The device of claim 1, wherein the composition further comprises at least one active agent or additive.

5. The device of claim 4, wherein the active agents comprise antimicrobial agents; antifungal agents, antiviral agents, growth factors, angiogenic factors, anaesthetics, mucopolysaccharides or wound healing proteins.

6. The device of claim 5, wherein the antimicrobial agents comprise isoniazid; ethambutol; pyrazinamide; streptomycin; clofazimine; rifabutin; fluoroquinolones; ofloxacin; sparfloxacin; rifamin; azithromycin; clarithromycin; dapsone; tetracycline; erythromycin; ciprofloxacin; doxycycline; ampicillin; amphotericin B; ketoconazole; fluconazole; pyrimethamine; sulfadiazine; clindamycin; lincomycin; pentamidine; atovaquone; paromomycin; diclarazil; acyclovir; trifluorouridine; foscarnet; penicillin; gentamicin; ganciclovir; iatroconazole; miconazole; zinc-pyrithione; heavy metals including but not limited to platinum or gold, or their combined forms including salts such as halides, saccharinates or complexes with carriers or other forms; or nanoparticles of silver, zinc or copper.

7. The device of claim 1, wherein hydrogen peroxide is present at a concentration of from about 0.01% to about 10%.

8. An antimicrobial composition comprising silver saccharinate, and wherein the composition is resistant to discoloration by heat and light, wherein the molar ratio of saccharinate to silver is between 1 and 1.5, and wherein the silver saccharinate is a compound formed from a chemical reaction between a silver salt and a saccharinate salt.

9. The composition of claim 8, wherein the composition further comprises suspensions, lotions, creams, ointments, jellies, gels, pessaries, inorganic carriers, porous glasses, oxides, silicates, talc, mica, silica, titania, zirconia, insoluble polymeric microspheres, hydroxy apatite, cellulose powder, chitin, chitosan, cross-linked polymers or topical gels.

10. The composition of claim 8, wherein the composition further comprises at least one active agent or additive.

11. The composition of claim 10, wherein the active agents comprise antimicrobial agents, antifungal agents, antiviral agents, growth factors, angiogenic factors, anaesthetics, mucopolysaccharides or wound healing proteins.

12. The composition of claim 11, wherein the antimicrobial agents comprise isoniazid; ethambutol; pyrazinamide; streptomycin; clofazimine; rifabutin; fluoroquinolones; ofloxacin; sparfloxacin; rifampin; azithromycin; clarithromycin; dapsone; tetracycline; erythromycin; ciprofloxacin; doxycycline; ampicillin; amphotericin B; ketoconazole; fluconazole; pyrimethamine; sulfadiazine; clindamycin; lincomycin; pentamidine; atovaquone; paromomycin; diclarazil; acyclovir; trifluorouridine; foscarnet; penicillin; gentamicin; ganciclovir; iatroconazole; miconazole; zinc-pyrithione; heavy metals including but not limited to platinum or gold, or their combined forms including salts such as halides, saccharinates or complexes with carriers or other forms; or nanoparticles of silver, zinc or copper.

13. The composition of claim 8, wherein hydrogen peroxide is present at a concentration of from about 0.01% to about 10%.

* * * * *